(12) United States Patent
Kawaura et al.

(10) Patent No.: US 7,875,052 B2
(45) Date of Patent: Jan. 25, 2011

(54) TISSUE CLOSURE AND TISSUE CLOSING DEVICE

(75) Inventors: Masakatsu Kawaura, Kanagawa (JP); Tomoji Maruyama, Kanagawa (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 530 days.

(21) Appl. No.: 11/304,704

(22) Filed: Dec. 16, 2005

(65) Prior Publication Data

US 2006/0135991 A1 Jun. 22, 2006

(30) Foreign Application Priority Data

Dec. 17, 2004 (JP) ............................. 2004-366780

(51) Int. Cl.
  *A61B 17/08* (2006.01)
  *A61B 17/04* (2006.01)
(52) U.S. Cl. ....................... 606/213; 606/232
(58) Field of Classification Search ................ 606/213, 606/232, 157, 158
See application file for complete search history.

(56) References Cited

U.S. PATENT DOCUMENTS

| | | | |
|---|---|---|---|
| 3,874,388 A | 4/1975 | King et al. | |
| 4,917,089 A * | 4/1990 | Sideris | 606/215 |
| 4,920,618 A | 5/1990 | Iguchi | |
| 5,222,974 A | 6/1993 | Kensey et al. | |
| 5,350,399 A | 9/1994 | Erlebacher et al. | |
| 5,411,520 A * | 5/1995 | Nash et al. | 606/213 |
| 5,531,759 A * | 7/1996 | Kensey et al. | 606/213 |
| 5,593,422 A | 1/1997 | Muijs Van de Moer et al. | |
| 5,662,681 A * | 9/1997 | Nash et al. | 606/213 |
| 5,676,689 A * | 10/1997 | Kensey et al. | 606/213 |
| 5,690,674 A | 11/1997 | Diaz | |
| 5,700,277 A * | 12/1997 | Nash et al. | 606/213 |
| 5,702,421 A * | 12/1997 | Schneidt | 606/213 |
| 5,853,422 A | 12/1998 | Huebsch et al. | |
| 6,312,446 B1 | 11/2001 | Huebsch et al. | |
| 6,315,787 B1 | 11/2001 | Tsugita et al. | |
| 6,508,828 B1 * | 1/2003 | Akerfeldt et al. | 606/215 |

(Continued)

FOREIGN PATENT DOCUMENTS

EP 0 362 113 A1 4/1990

(Continued)

*Primary Examiner*—(Jackie) Tan-Uyen T Ho
*Assistant Examiner*—Jing Rui Ou
(74) *Attorney, Agent, or Firm*—Buchanan Ingersoll & Rooney PC

(57) ABSTRACT

A tissue closure includes a body, and a thread includes a knot which is slidable on the thread. The body is composed of a plate-like anchor portion, and a deformation portion having a frame-like shape which can be deformed between a first form in which the deformation portion is elongated in a direction substantially perpendicular to the anchor portion and contracted in a direction substantially parallel to the anchor portion and a second form in which the deformation portion is contracted in a direction substantially perpendicular to the anchor portion and elongated in a direction substantially parallel to the anchor portion. The tissue closure can also include a connecting portion connecting the anchor portion and the deformation portion to each other. In the condition where the deformation portion is in a desired form between the first form and the second form, the condition is maintained by the thread.

20 Claims, 21 Drawing Sheets

U.S. PATENT DOCUMENTS

| | | |
|---|---|---|
| 6,749,622 B2 * | 6/2004 | McGuckin et al. ........... 606/213 |
| 6,780,197 B2 * | 8/2004 | Roe et al. .................... 606/213 |
| 6,783,499 B2 * | 8/2004 | Schwartz .................... 600/486 |
| 2002/0173820 A1 | 11/2002 | Akerfeldt et al. |
| 2003/0093096 A1 * | 5/2003 | McGuckin et al. ........... 606/157 |
| 2003/0144695 A1 * | 7/2003 | McGuckin et al. ........... 606/213 |
| 2004/0002681 A1 | 1/2004 | McGuckin, Jr. et al. |
| 2004/0073242 A1 * | 4/2004 | Chanduszko ................ 606/157 |
| 2004/0116949 A1 * | 6/2004 | Ewers et al. ................ 606/167 |
| 2004/0133236 A1 * | 7/2004 | Chanduszko ................ 606/213 |
| 2004/0143294 A1 * | 7/2004 | Corcoran et al. ............ 606/213 |

FOREIGN PATENT DOCUMENTS

| | | |
|---|---|---|
| JP | 59-180109 | 10/1984 |
| JP | 1-87310 | 6/1989 |
| JP | 5-22824 | 3/1993 |
| JP | 5-212038 | 8/1993 |
| JP | 2002-360584 | 12/2002 |
| WO | WO 2005/063133 A1 | 7/2005 |

* cited by examiner

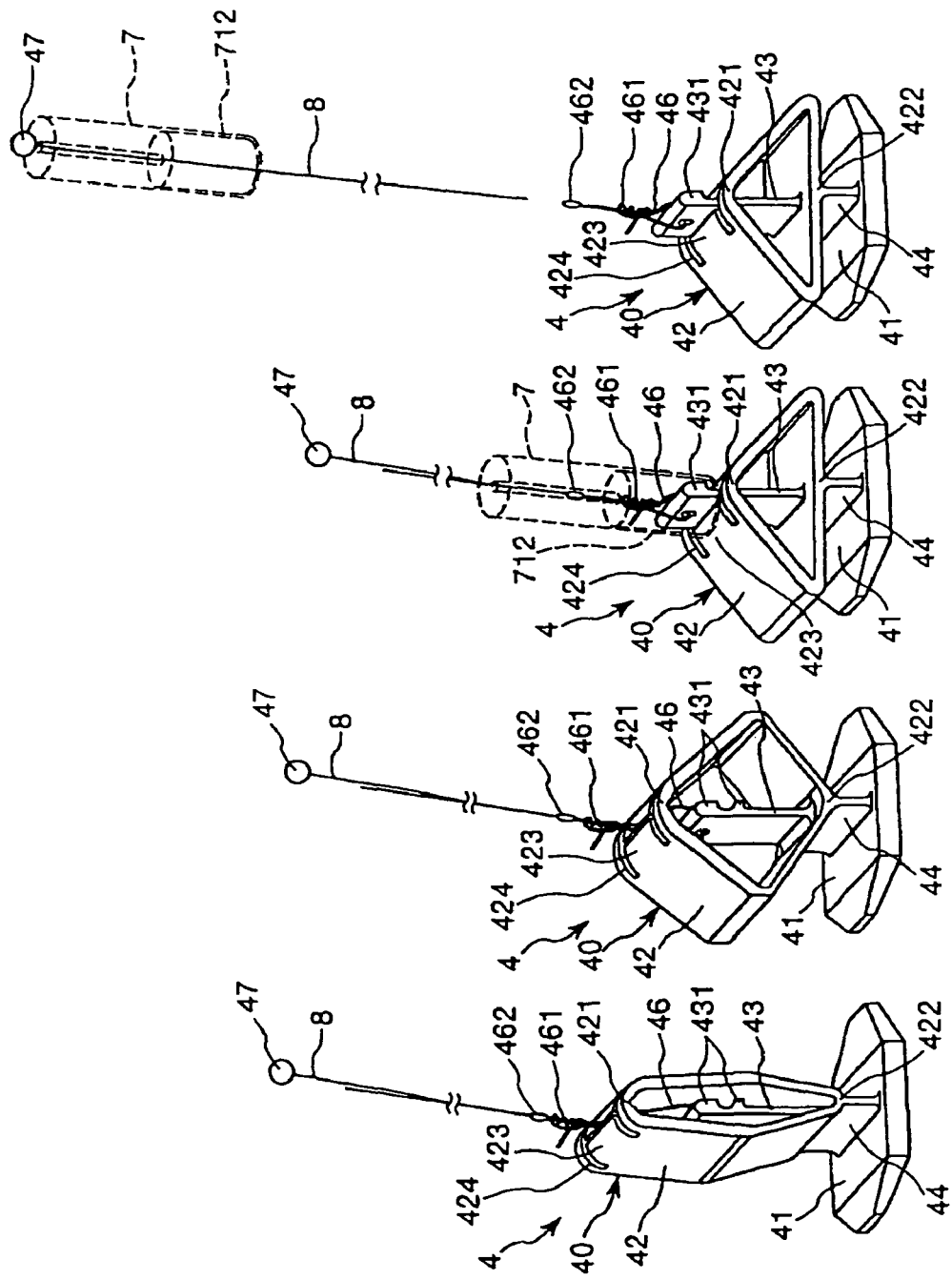

TISSUE CLOSURE AND TISSUE CLOSING DEVICE

FIELD OF THE INVENTION

The present invention generally relates to devices used in medical treatment or a medical procedure. More particularly, the present invention pertains to a tissue closure and a tissue closing device.

BACKGROUND DISCUSSION

Low-invasion operations involving inserting a device for diagnosis or therapy such as a catheter into a blood vessel or some other in vivo tissue are known. For example, in the treatment (diagnosis or therapy) of the coronary artery of the heart, it is necessary to insert a device such as a catheter into a blood vessel in order to perform the diagnosis or therapy treatment.

Such insertion of a catheter into a blood vessel is normally performed through a puncture formed by dissecting the femoral region. Accordingly, after the treatment is completed, it is necessary to stanch the bleeding from the puncture. However, since the blood pressure upon bleeding (bleeding blood pressure) from the femoral artery is relatively high, a person involved in the medical treatment must continue to hold down or apply pressure to the required part for a relatively long period of time using his/her finger.

In recent years, in order to perform such a stanching work more easily and reliably, a variety of devices have been developed for insertion through a wound hole to close a hole formed in a blood vessel. Examples of these devices are disclosed in U.S. Pat. No. 5,690,674 and U.S. Pat. No. 5,593,422.

U.S. Pat. No. 5,690,674 discloses a device for closing a hole formed in a blood vessel, wherein two flexible disk-like members are integrated so that they are connected at their central portions. This device is invariable of the positional relationship of the two disk-like members and is fixed by the flexibility of the two disk-like members in the wound hole.

A patient subjected to a catheter treatment and a test on the heart or the like may have blood vessel disease at a location other than the heart, and a blood vessel lesion may be present also in the femoral artery through which a catheter is inserted. For example, the blood vessel wall thickness of the femoral artery through which the catheter is inserted is about 1 mm in the case of a healthy blood vessel, but there may be cases where the blood vessel has been thickened to a wall thickness of 2 mm or more, or where the blood vessel wall has become hard through calcification. In addition, in a patient having received a catheter procedure a plurality of times, the periphery of a punctured portion of a blood vessel may have become fibrous and turned into a hard vestigium. Besides, the size of a wound formed by the insertion of a catheter differs for individual patients depending on the elasticity, wall thickness, lesion or the like of the blood vessel. Thus, there are sometimes significant differences between different patients concerning the conditions (status) of the blood vessel and the surrounding tissues of the patient in which a catheter is left to indwell.

U.S. Pat. No. 5,593,422 discloses a device in which a closing member to which a thread is attached is disposed in a blood vessel and a ring (locking member) is moved along the thread. Then ring locks the thread outside the blood vessel to close up the hole formed in the blood vessel. In the case of this device, the closing member is secured to the wall of the blood vessel by fixing the ring to the thread in some way.

Therefore, with the device disclosed in U.S. Pat. No. 5,593,422, an operation of securing the ring to the thread within subcutaneous tissues is needed. Further, after the ring is secured to the thread, it is necessary to perform an operation of cutting the thread within the subcutaneous tissues.

Furthermore, since the outside diameter of the ring needs be of a dimension allowing the ring to be inserted into the wound hole, the ring must be formed in a small size, and there is the possibility that the ring may drop into the blood vessel through the hole formed in the blood vessel.

SUMMARY

According to one aspect of the present invention, a tissue closure for closing an opening on a wall of living body cavity comprises a plate-shaped anchor portion adapted to be held at and around the opening from one side of the wall of the living body cavity, and a deformation portion comprising a frame-shaped body. The deformation portion is deformable between a first form in which the body is elongated in a direction substantially perpendicular to the anchor portion and contracted in a direction substantially parallel to the anchor portion and a second form in which the body is contracted in a direction substantially perpendicular to the anchor portion and elongated in a direction substantially parallel to the anchor portion. In addition, a thread member is adapted to maintain the deformation portion in a desired form between the first form and the second form.

According to another aspect, a tissue closure for closing an opening on a wall of living body cavity comprises an anchor portion positionable at and around the opening on one side of the wall of the living body cavity, a deformation portion deformable between a first form in which the deformation portion is elongated in a direction substantially perpendicular to the anchor portion and a second form in which the deformation portion is compressed from the first form toward the anchor portion, and a thread member adapted to maintain the deformation portion in a desired form between the first form and the second form. The thread member is comprised of a double thread having one end portion thereof as a bent-back portion, and being disposed so that the deformation portion is located between the bent-back portion and the anchor portion. In addition, the bent-back portion forms a loop.

In accordance with another aspect, a tissue closing device comprises a tissue closure comprising an anchor portion, a deformation portion and a thread member, wherein the anchor portion is positionable at and around the opening on one side of the wall of the living body cavity, the deformation portion is deformable between a first form in which the deformation portion is elongated in a direction substantially perpendicular to the anchor portion and a second form in which the deformation portion is compressed from the first form toward the anchor portion, and the thread member maintains the deformation portion in a desired form between the first form and the second form. The tissue closure device also comprises an arrangement device possessing an elongate shape, with the arrangement device detachably retaining the tissue closure at a distal end portion thereof. The tissue closure is arranged in a living organism so as to close the opening by penetrating a tissue membrane of the wall with the tissue closure Another aspect involves a method of closing an opening on a wall of living body cavity comprising inserting a tissue closure through the opening on the wall of the living body cavity so that an anchor portion of the tissue closure is positioned on one side of the opening, and deforming a deformation portion of the tissue closure to compress the deformation portion in a direction toward the anchor portion while the deformation portion is on an opposite side of the opening from the anchor portion, with the anchor portion being positioned to cover and close off the opening.

BRIEF DESCRIPTION OF THE DRAWING FIGURES

The foregoing and additional features and characteristics of the disclosed subject matter will become more apparent from the following detailed description considered with reference to the accompanying drawing figures in which like reference numerals designate like elements.

Figure 1:
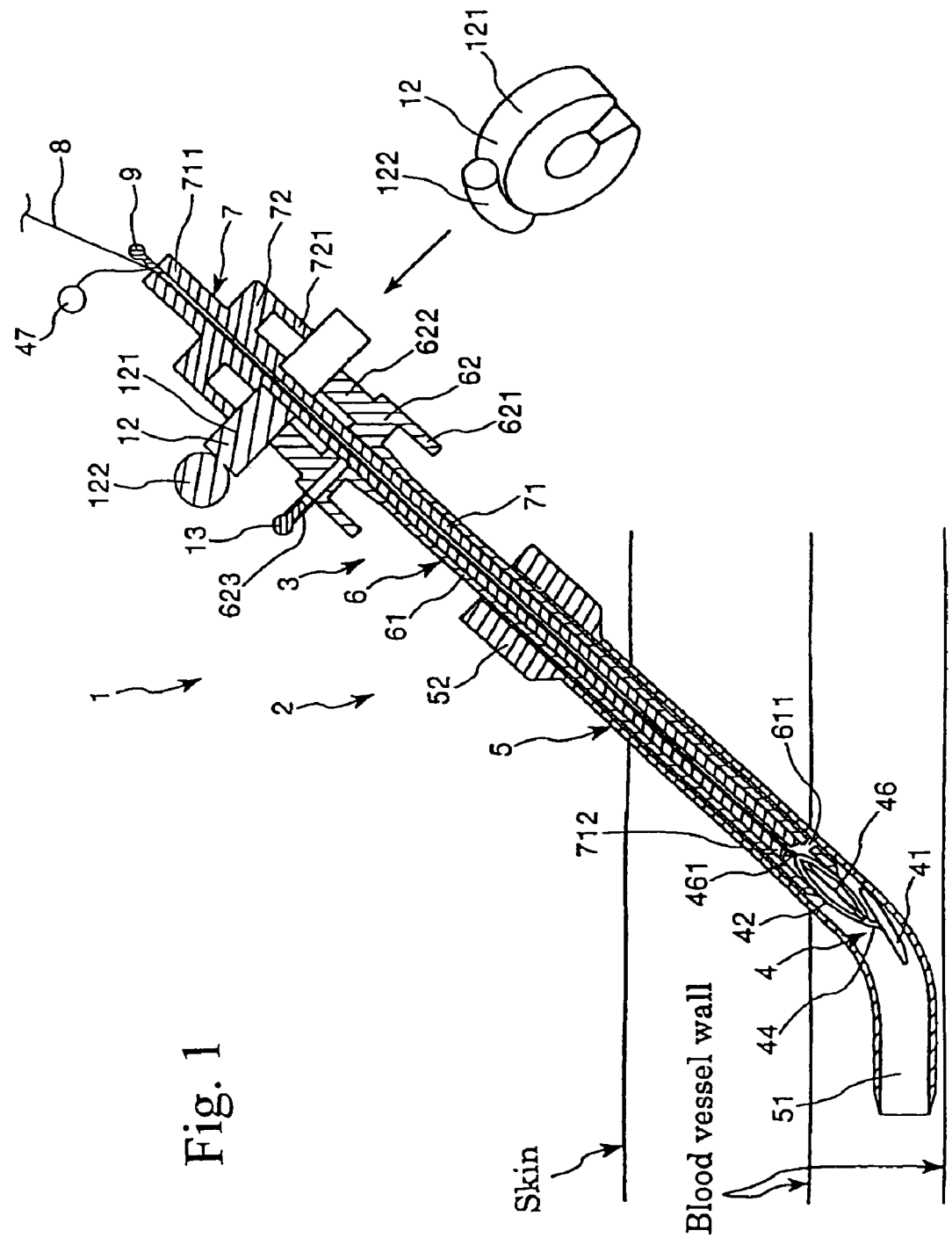
FIG. 1 is a cross-sectional view of one embodiment of the tissue closing device according to the present invention, including a tissue closure.
Figure 2:
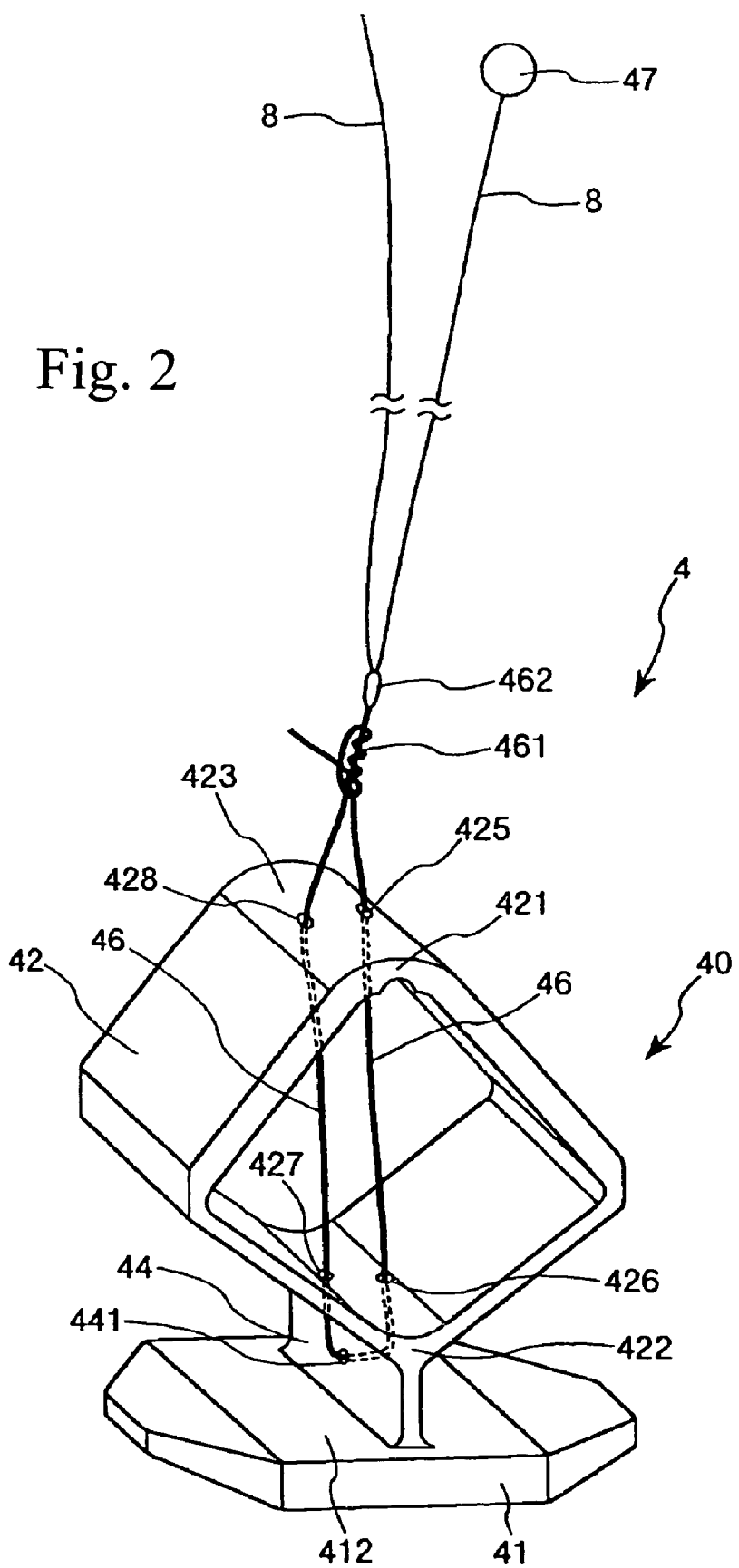
FIG. 2 is a perspective view of a tissue closure used in the tissue closing device shown in FIG. 1.

FIGS. 5(a)-5(d) are perspective views illustrating operations performed in using the tissue closing device and tissue closure shown in FIGS. 1 and 2.

Figure 6:
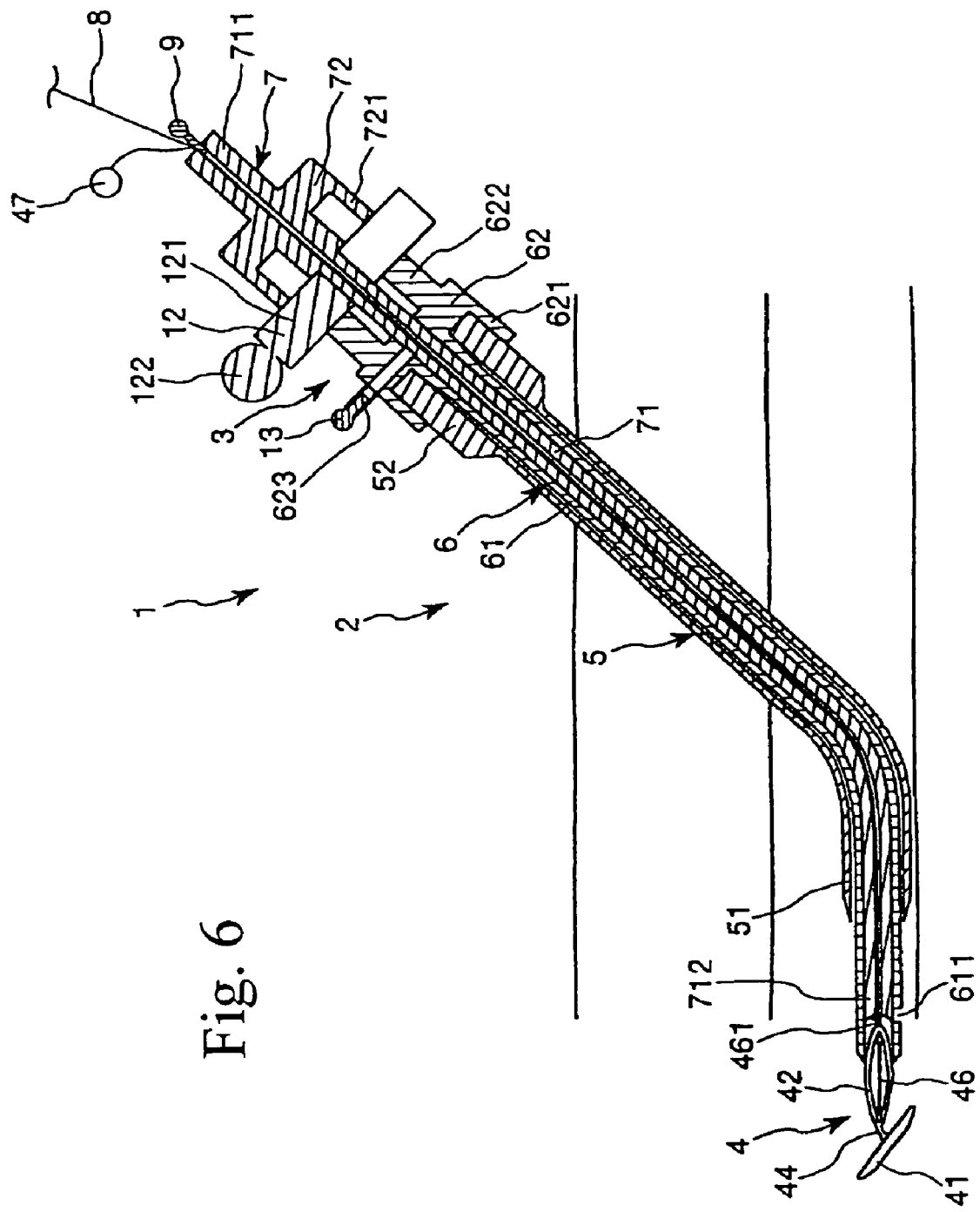

FIG. 6 is a cross-sectional view illustrating one operational aspect of the tissue closing device shown in FIG. 1.

Figure 7:
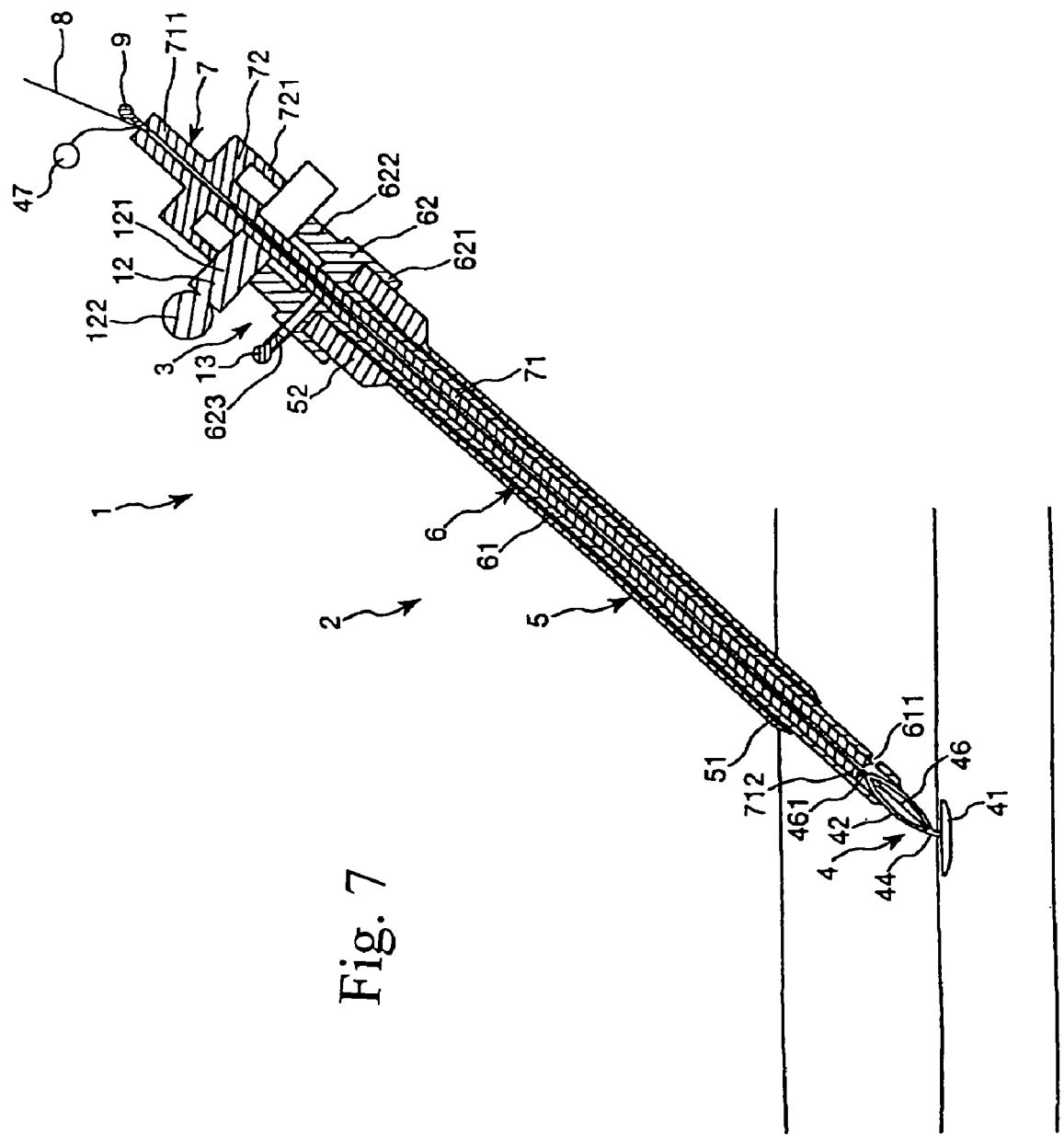

FIG. 7 is a sectional view illustrating another operational aspect of the tissue closing device shown in FIG. 1.

Figure 8:
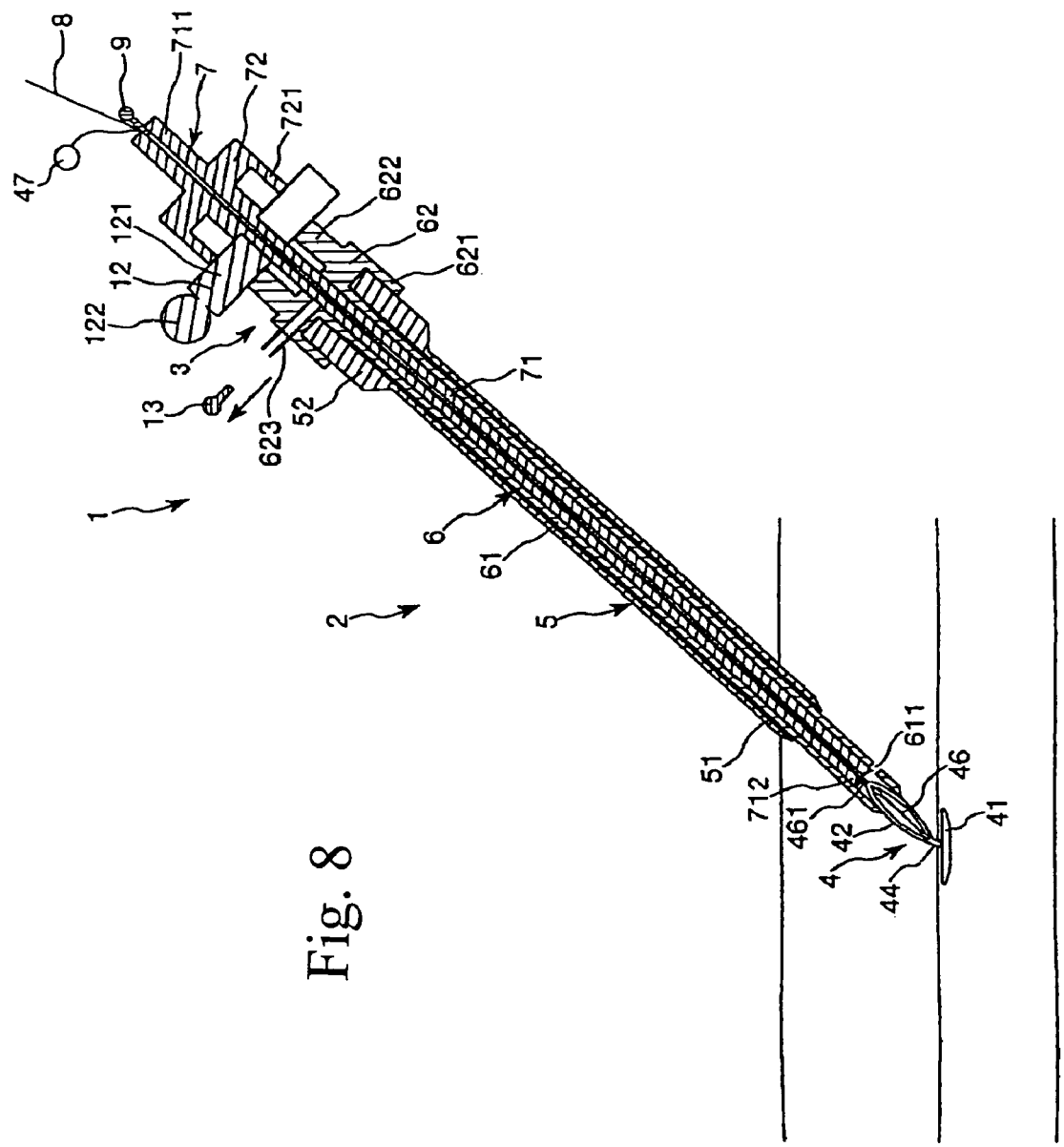

FIG. 8 is a sectional view illustrating another operational aspect of the tissue closing device shown in FIG. 1.

Figure 9:
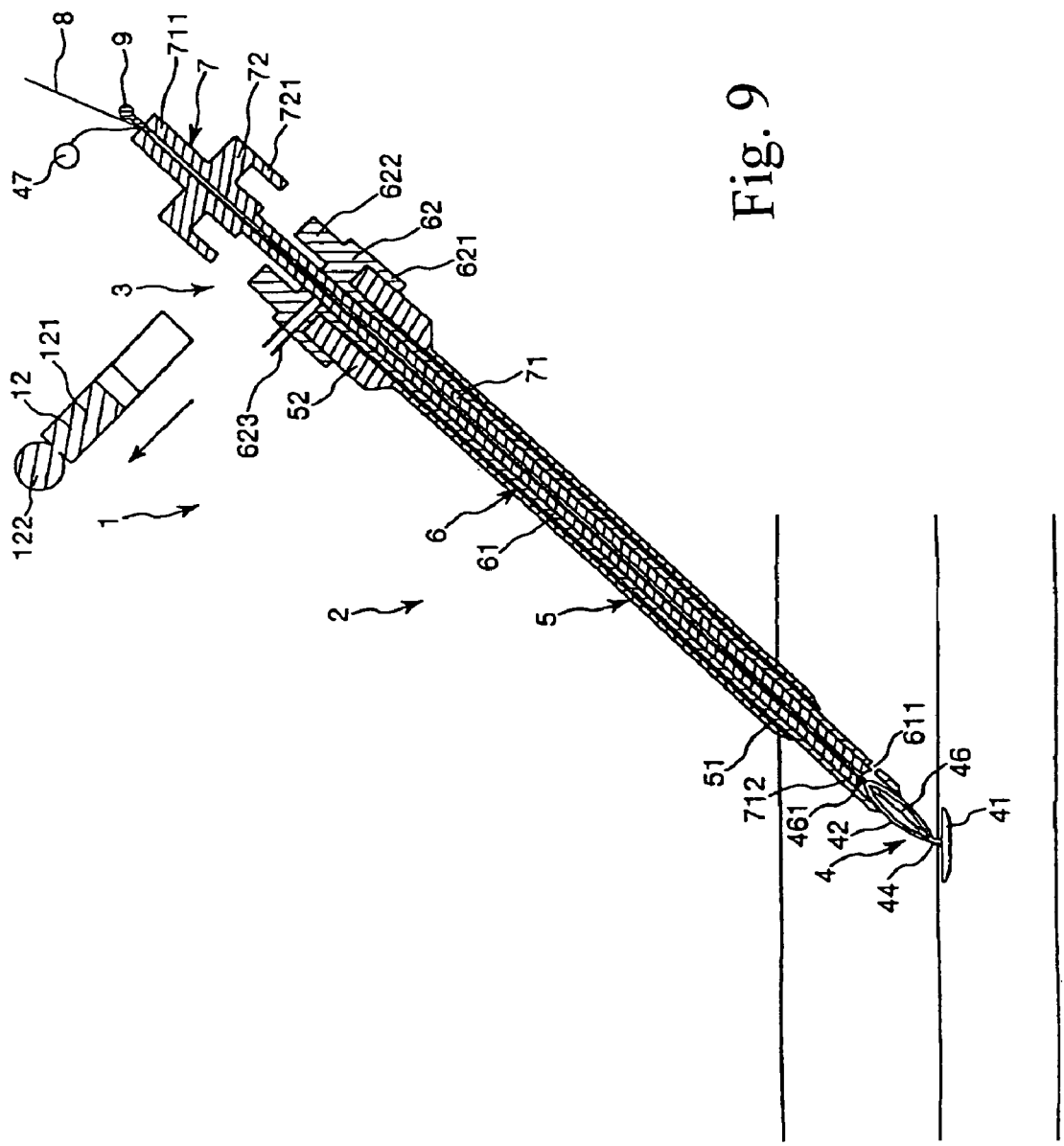

FIG. 9 is a sectional view illustrating another operational aspect of the tissue closing device shown in FIG. 1.

Figure 10:
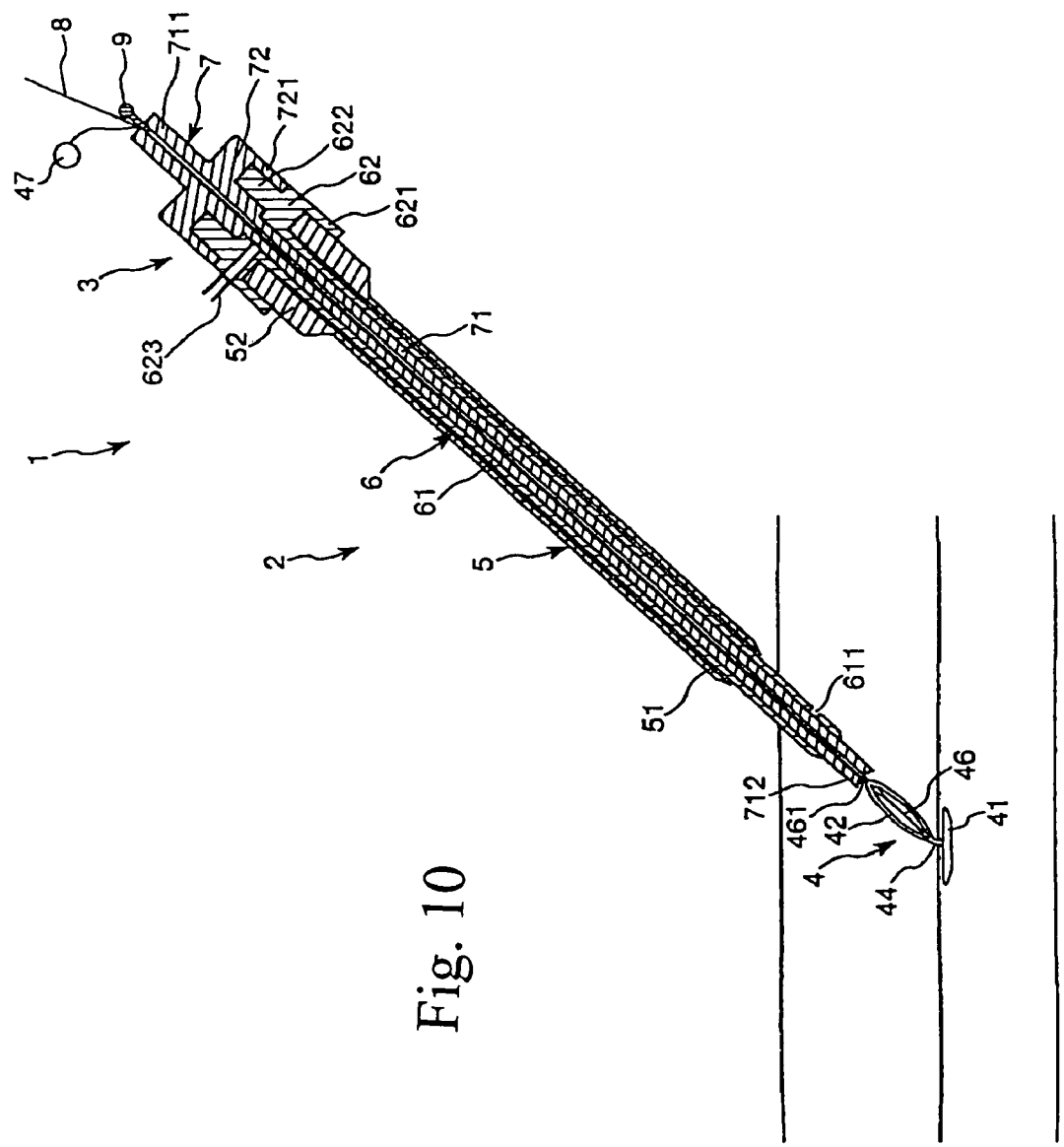

FIG. 10 is a sectional view illustrating another operational aspect of the tissue closing device shown in FIG. 1.

Figure 11:
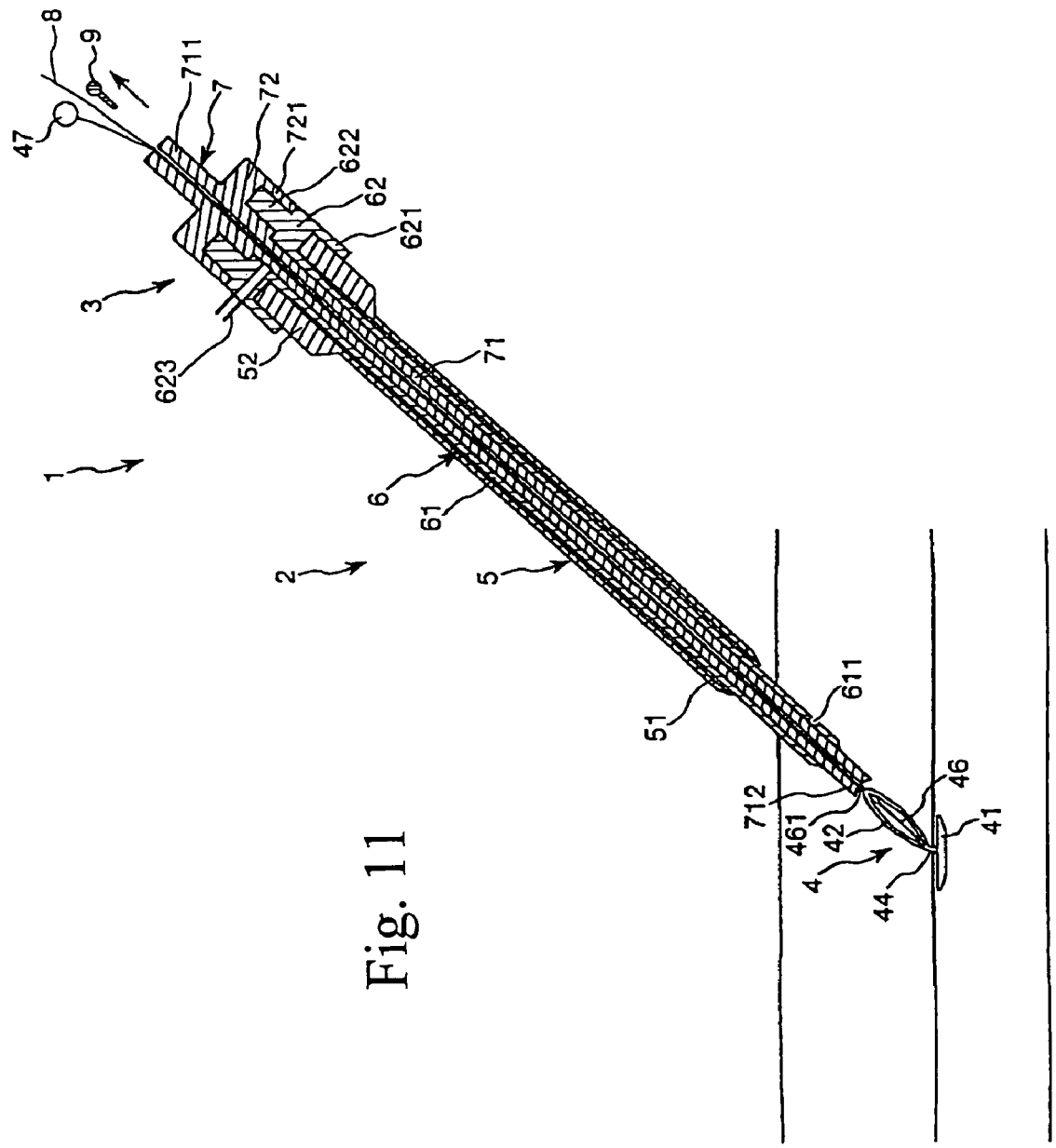

FIG. 11 is a sectional view illustrating another operational aspect of the tissue closing device shown in FIG. 1.

Figure 12:
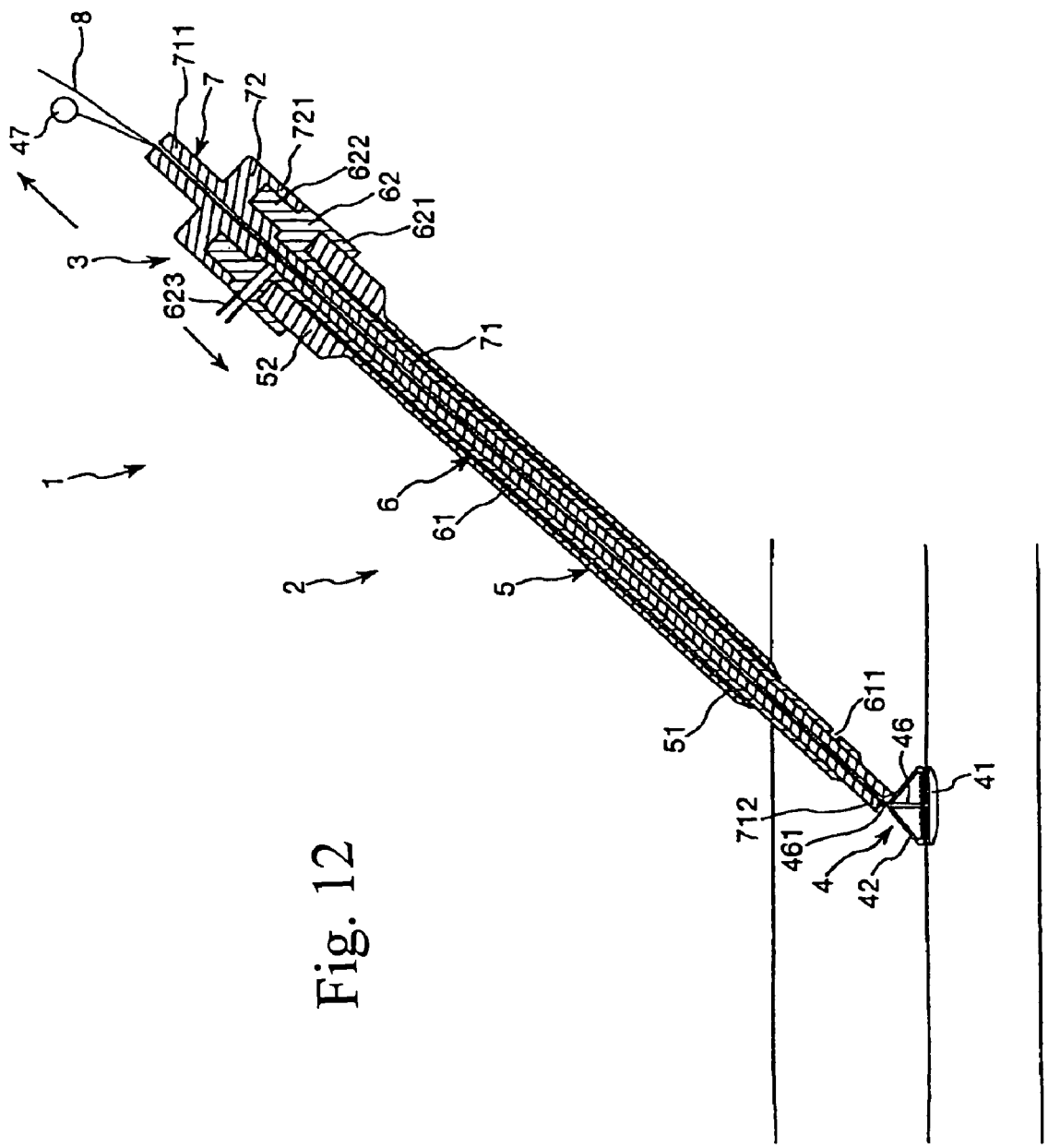

FIG. 12 is a sectional view illustrating another operational aspect of the tissue closing device shown in FIG. 1.

Figure 13:
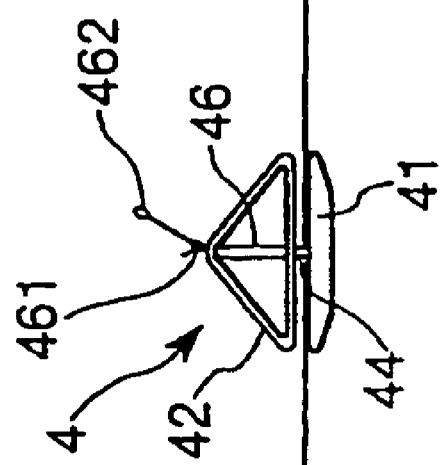

FIG. 13 is a sectional view illustrating another operational aspect of the tissue closing device shown in FIG. 1.

Figure 14:
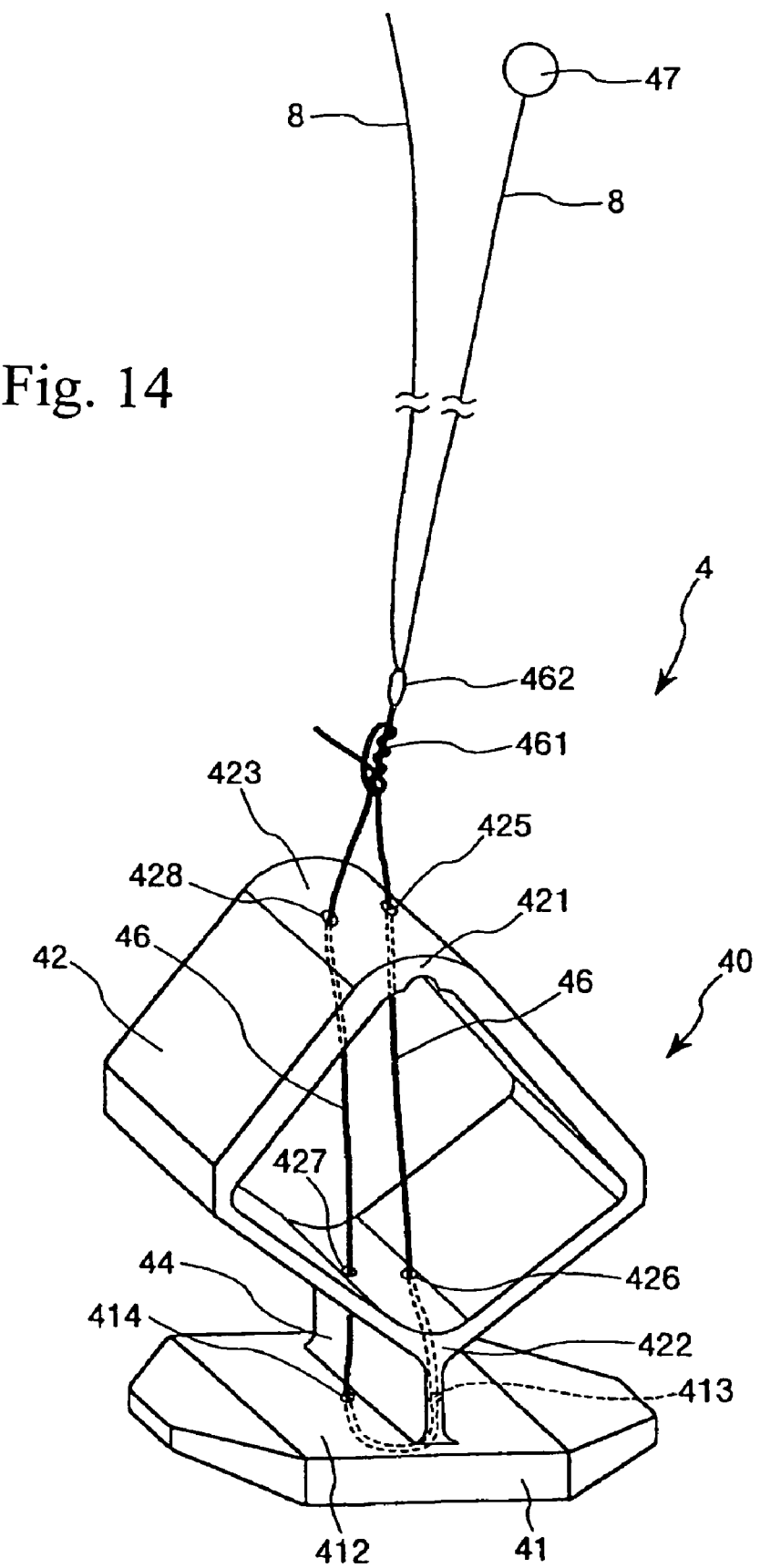

FIG. 14 is a perspective view of a second embodiment of a tissue closure used in the tissue closing device.

Figure 15:
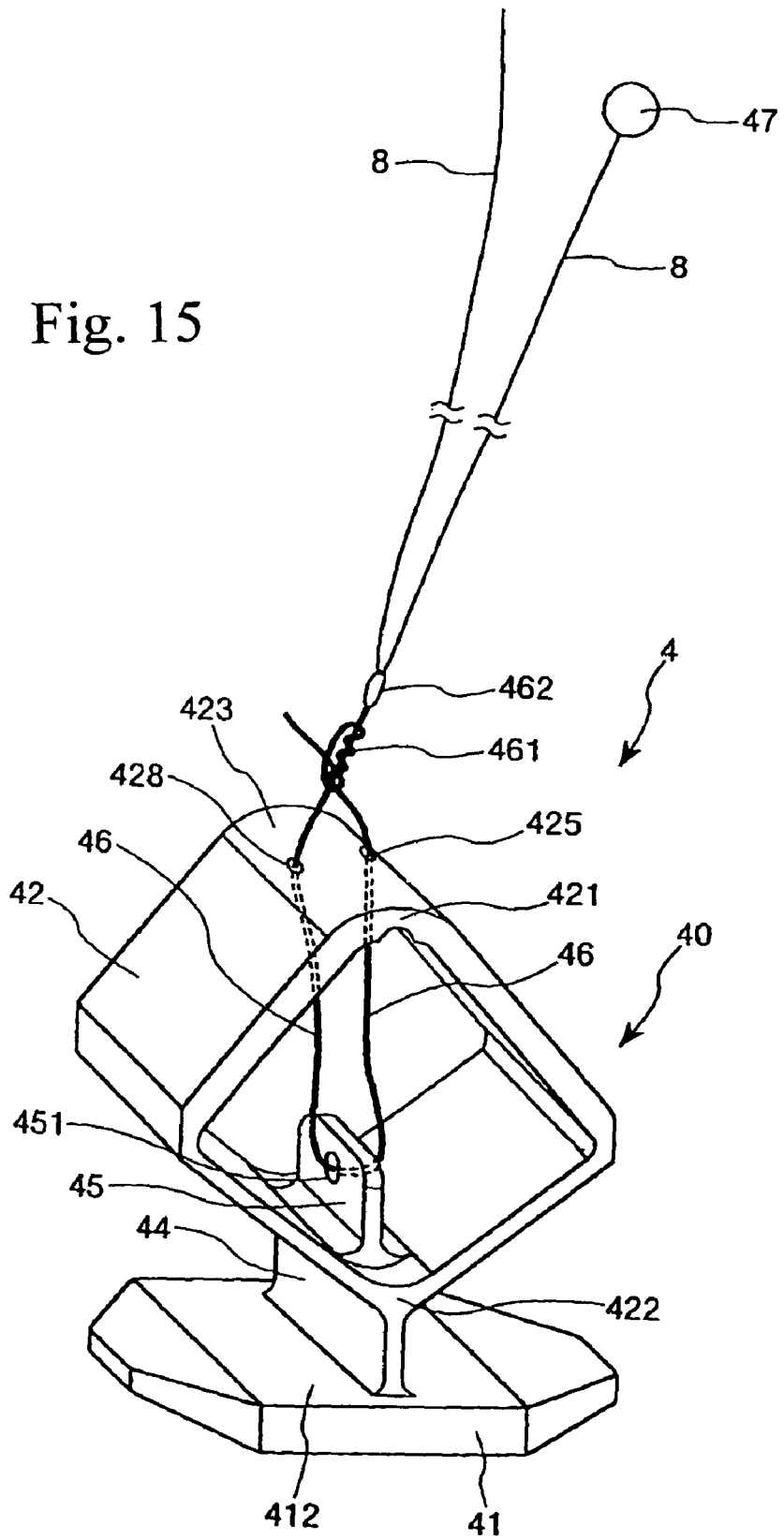

FIG. 15 is a perspective view of a third embodiment of the tissue closure used in the tissue closing device.

Figure 16:
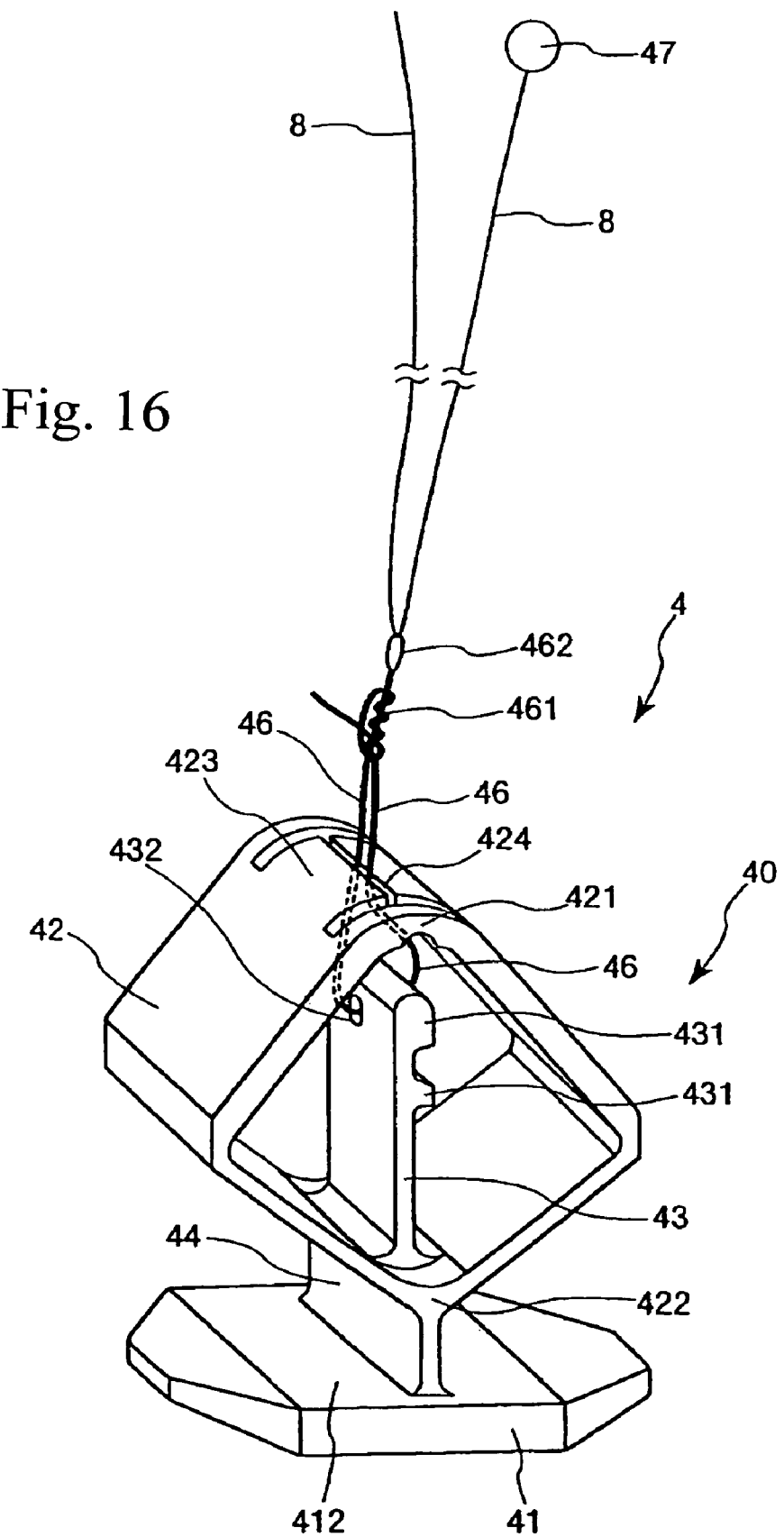

FIG. 16 is a perspective view of a fourth embodiment of a tissue closure used in the tissue closing device.

FIGS. 17(a) to 17(d) are perspective views illustrating operational aspects of the tissue closing device using the tissue closure shown in FIG. 16 together with a pusher tube.

Figure 18A:
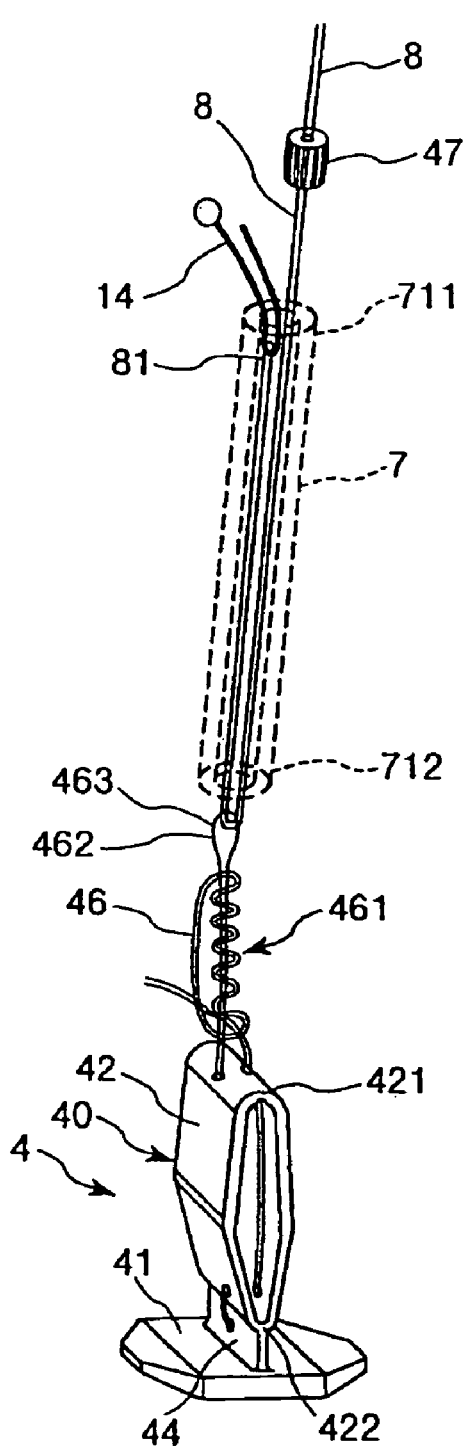
Figure 18B:
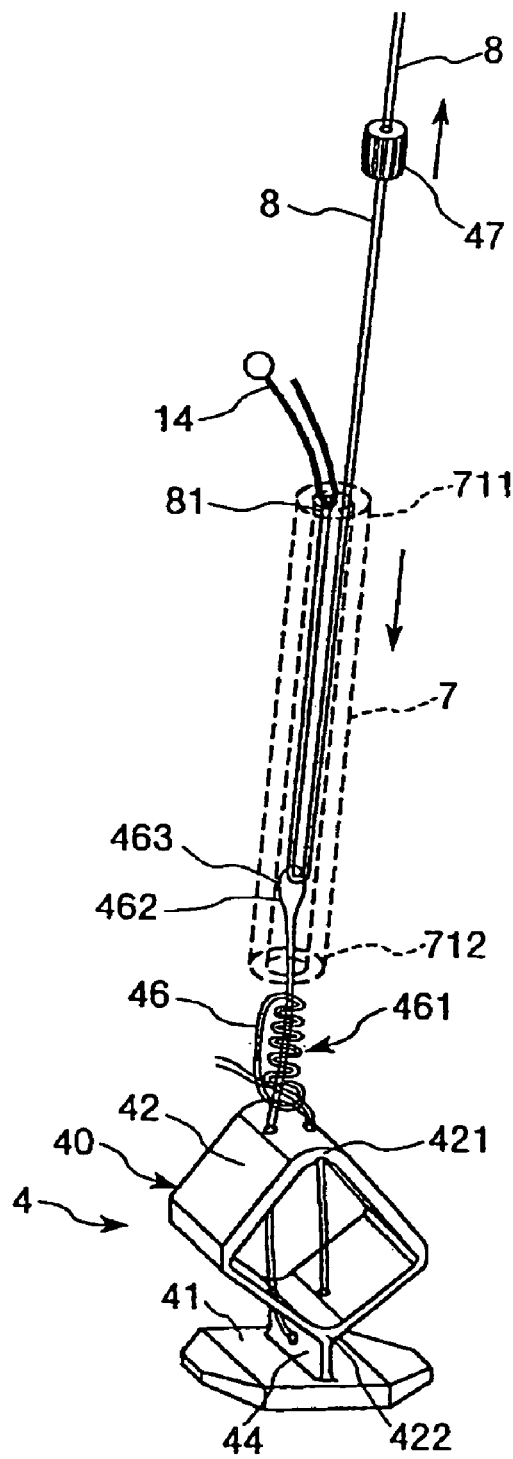

FIGS. 18(a) and 18(b) are perspective views of a fifth embodiment of the tissue closure illustrating operational aspects of the tissue closing device using the tissue closure together with a pusher tube.

Figure 19A:
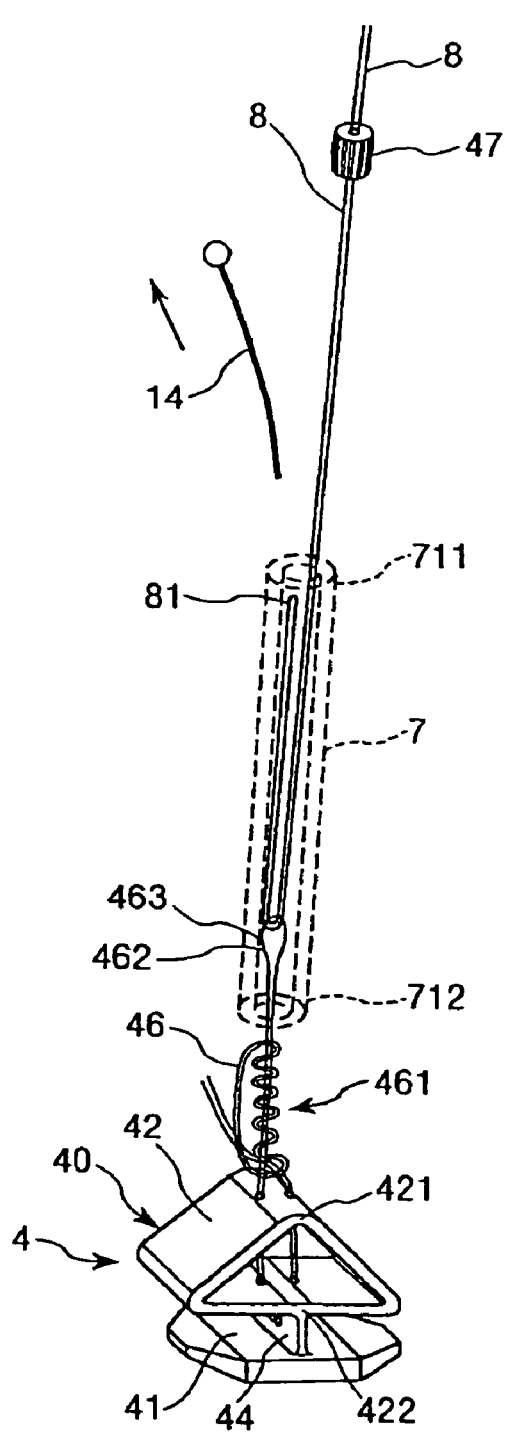
Figure 19B:
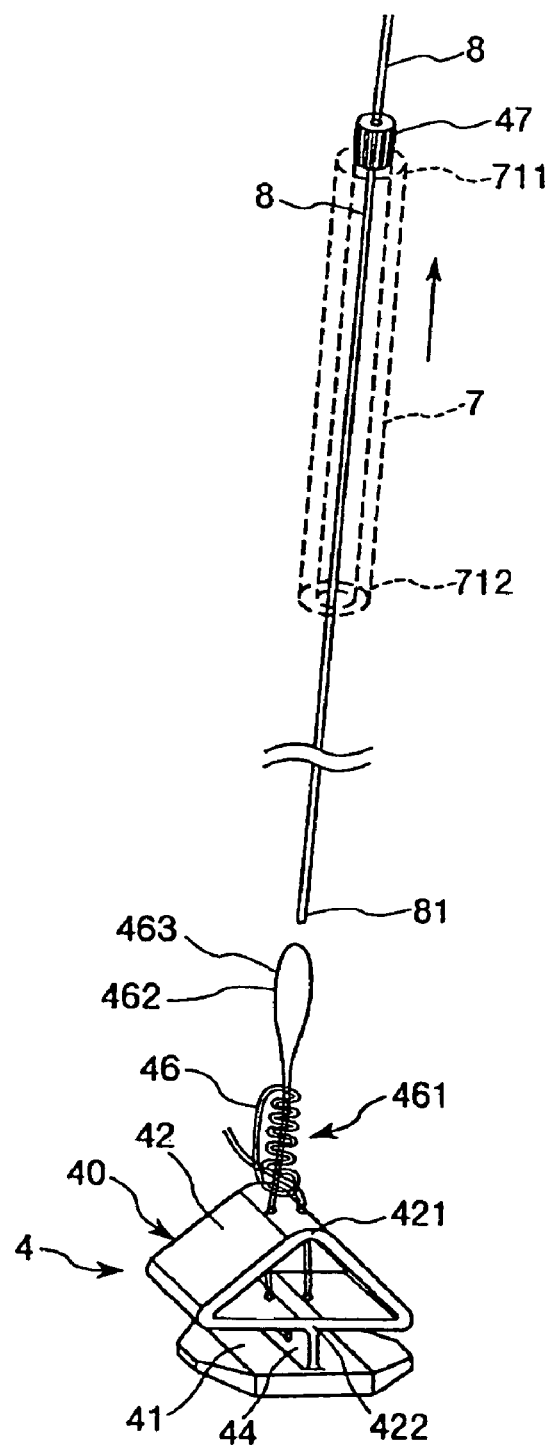

FIGS. 19(a) and 19(b) are perspective views showing additional operational aspects of the tissue closing device using the tissue closure shown in FIGS. 18(a) and 18(b).

Figure 20:
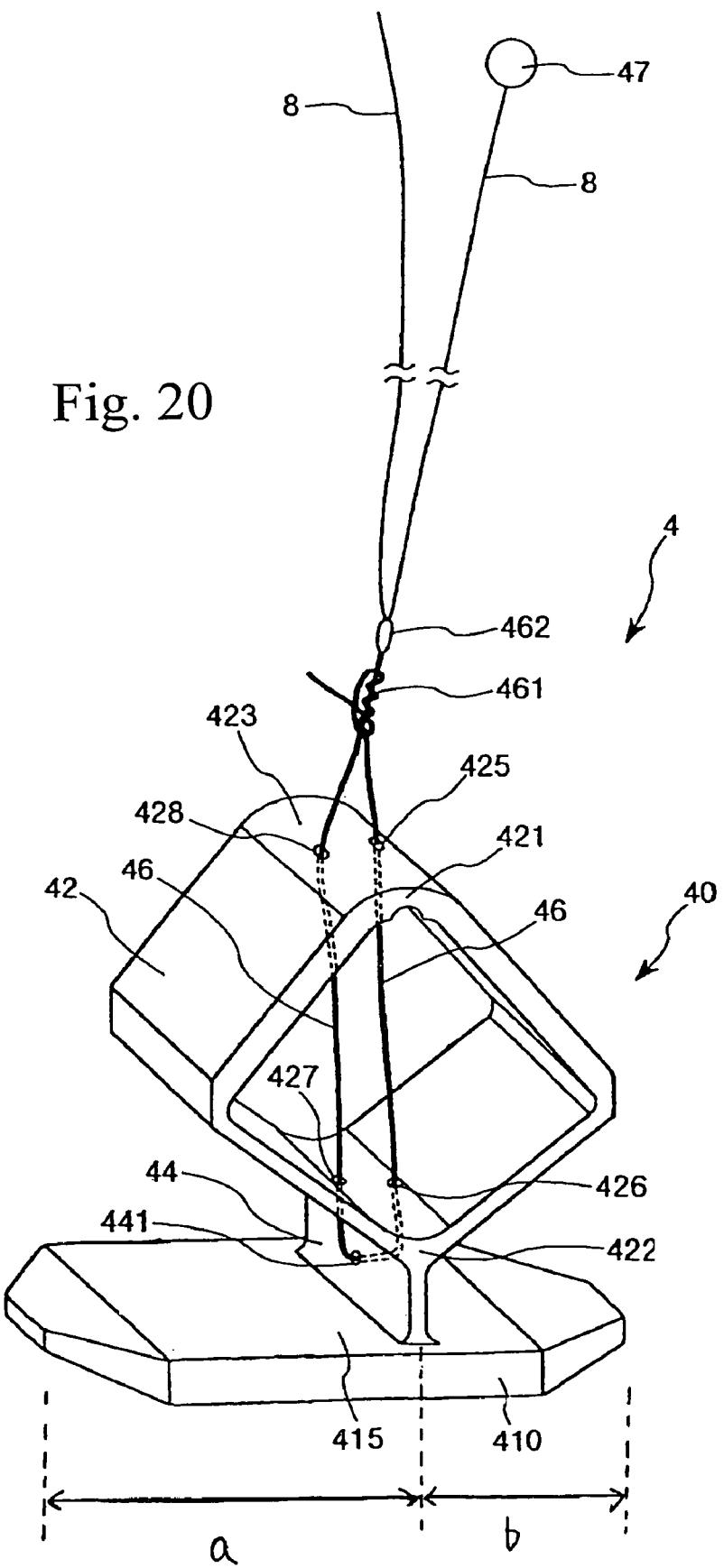

FIG. 20 is a perspective view of a sixth embodiment of a tissue closure used in the tissue closing device.

Figure 21:
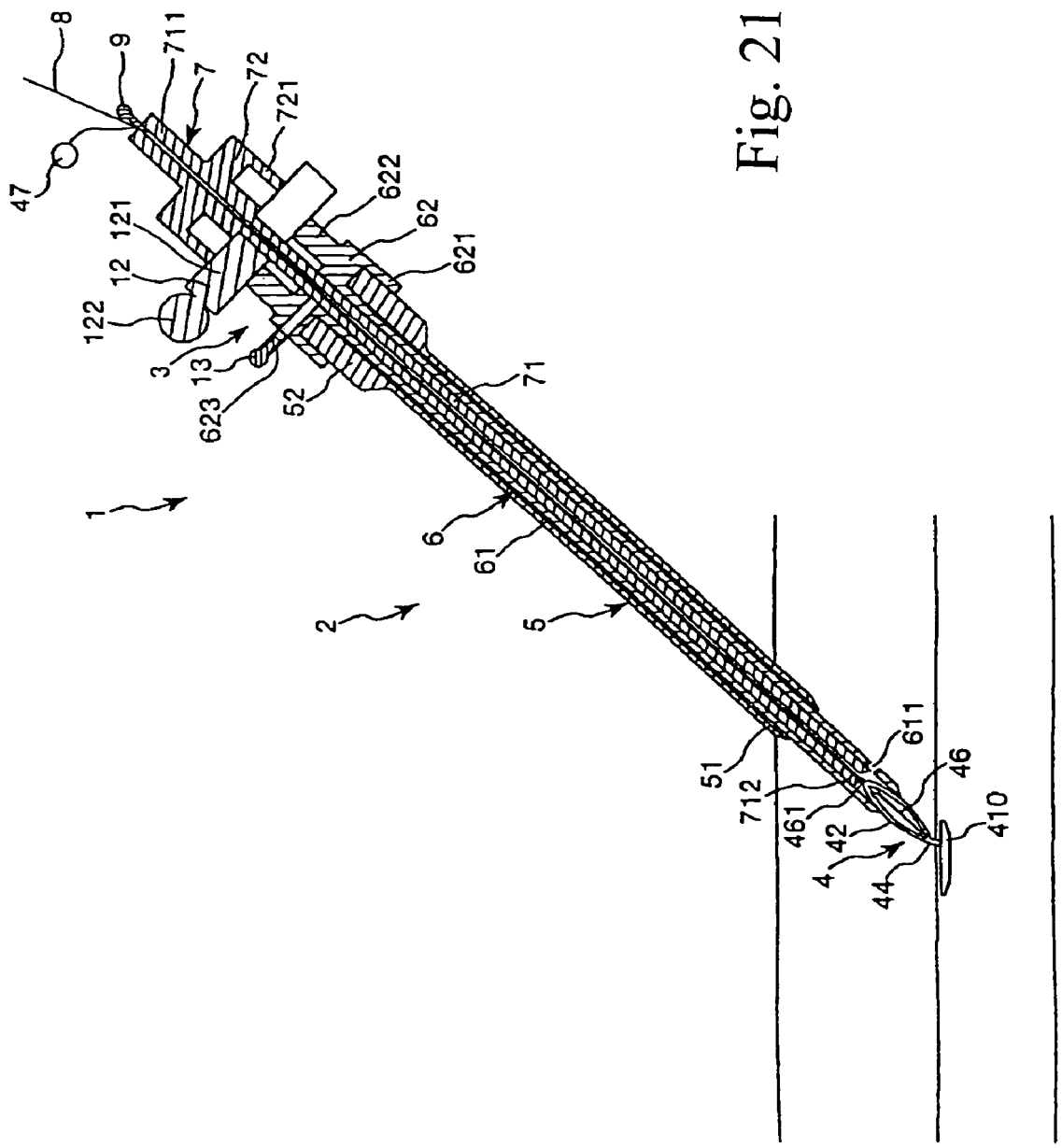

FIG. 21 is a sectional view illustrating an operational aspect of the tissue closing device using the tissue closure shown in FIG. 20.

DETAILED DESCRIPTION

The tissue closure and the tissue closing device according to the present invention will be described in detail below, based on preferred embodiments shown in the accompanying drawing figures.

Figure 3:
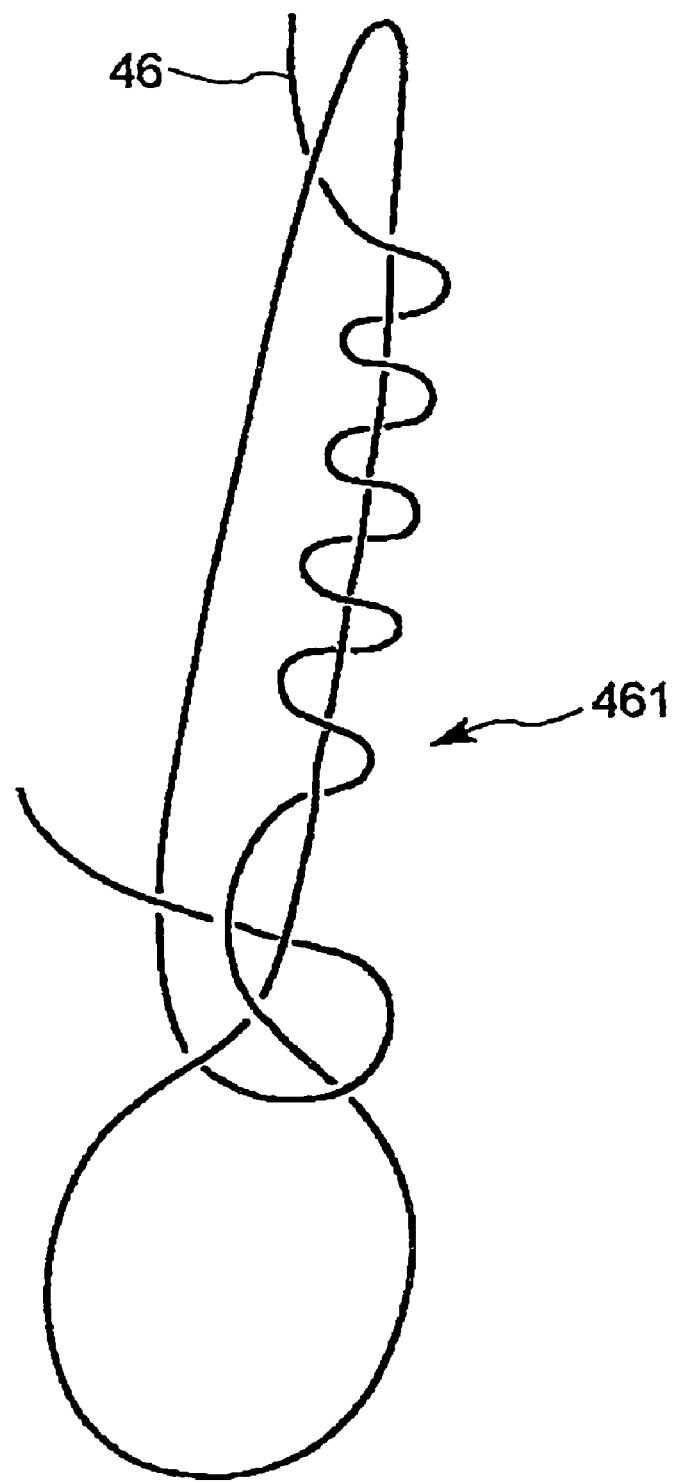
FIG. 3 is an illustration of one example of a knot used in the tissue closure shown in FIGS. 1 and 2.
Figure 4:
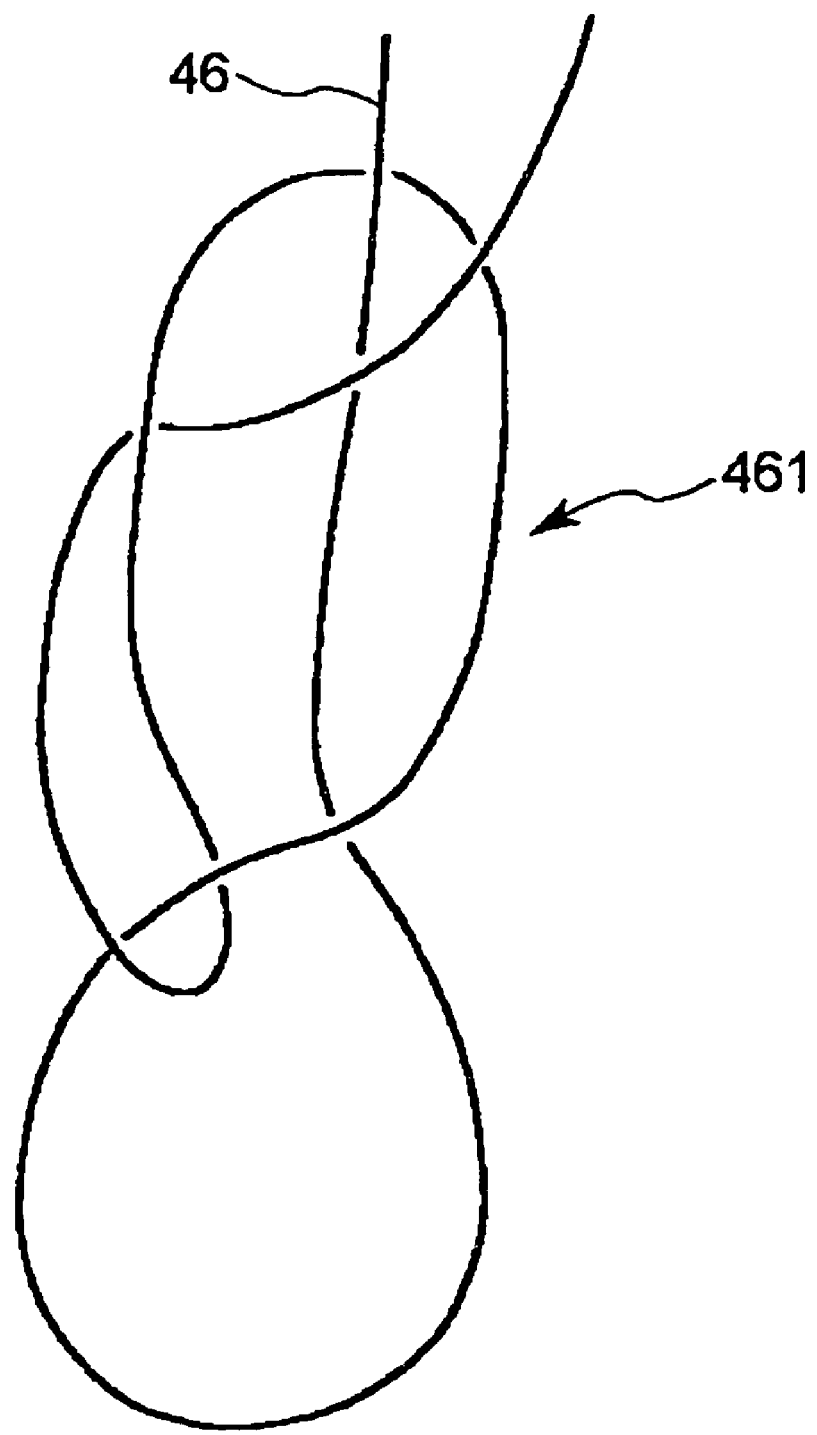
FIG. 4 is an illustration of another example of a knot used in the tissue closure shown in FIGS. 1 and 2.
Figure 5:
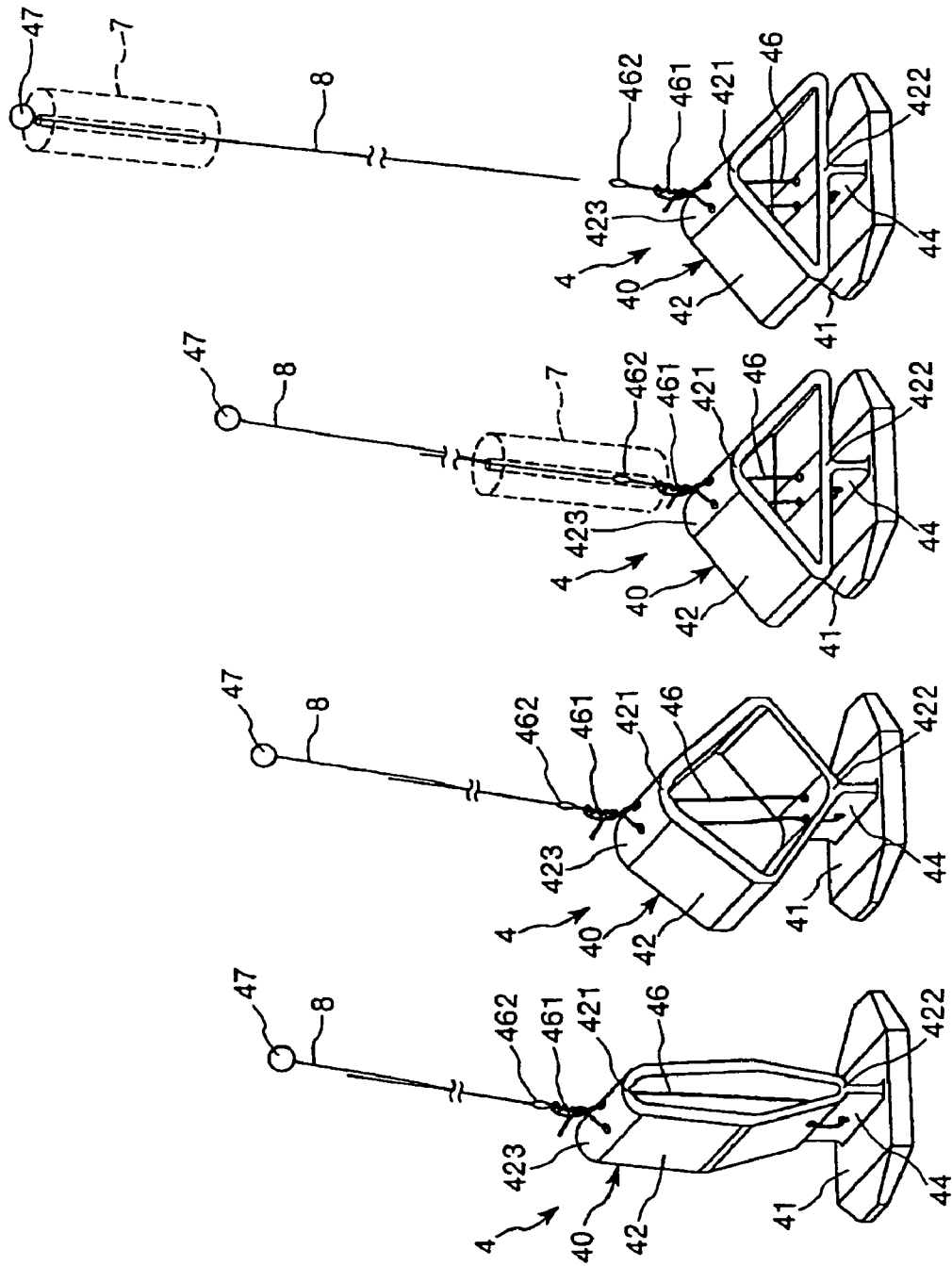

For convenience of description, in FIGS. 1 and 6-12, the left lower side in the drawings will be referred as "distal" and the right upper side will be referred to as "proximal", and in FIGS. 2-5 and 13, the upper side in the drawings will be referred to as "proximal" and the lower side will be referred to as "distal". It is to be noted that FIG. 1 illustrates a perspective view of a stopper 12 and FIG. 5 schematically illustrates a pusher tube 7 in broken lines.

The tissue closing device 1 shown in the drawing figures and described in more detail below is a device for closing (closing up) an undesirable opening such as a wound hole formed on a living body cavity wall as an in vivo tissue membrane, for example, a living organism lumen such as a blood vessel, an internal organ of a living organism, and an internal tissue of a living organism, and is percutaneously penetrating (a wound hole penetrating an in vivo tissue lumen).

As shown in FIGS. 1 and 2, the tissue closing device 1 includes a clip 4, forming a tissue closure for closing an undesirable opening such as a wound hole penetrating an in vivo tissue membrane of a living body cavity wall, and a clip delivery assembly comprising an elongate body portion 2 and a thread (second thread member) forming a pulling means for pulling the clip 4. The clip 4 is detachably mounted (retained) in a distal end portion of the body portion 2.

The body portion 2 includes a sheath 5 provided with a through-hole 51 passing through its central portion in the axial direction, and an elongated arrangement device 3, forming a feeding and deformation means, which is detachably mounted in the sheath 5 (e.g., is inserted in the sheath 5). At the time of a stanching operation (an operation or work to close a wound hole), distal end portions of the sheath 5 and the arrangement device 3 and the clip 4 penetrate the wound hole, respectively. Namely, they are inserted into a living body cavity (lumen of a living organism) such as a blood vessel via a wound hole.

The sheath 5 has a roughly hollow cylindrical shape, and is provided with a hub 52 at its proximal end portion. In addition, a hemostatic valve (not shown) is disposed on the inner circumferential side of the hub 52.

Examples of the sheath 5 include a sheath (introducer sheath) left indwelling after a treatment for therapy (such as Percutaneous Coronary Intervention: PCI) or diagnosis (such as Coronary AngioGraphy: CAG) using a catheter. Also, a sheath for exclusive use in the tissue closing device 1 may be used.

Incidentally, while the components of the body portion 2 include the sheath 5 in this embodiment, the components of the body portion 2 need not necessarily include the sheath 5.

The arrangement device 3 includes an outer tube 6 (tubular member) which is an elongated tubular member, a pusher tube 7 (tubular member) which is an elongated tubular member adapted to be detachably mounted in or inserted into the outer tube 6, a cap 9 forming a thread-retaining member, a cap 13 forming a port-closing member for position confirmation, and a stopper 12. The outer tube 6 and the pusher tube 7 constitute a major portion of the arrangement device 3 forming a feeding means for feeding the clip 4 and a deformation means for deforming a deformation portion 42 by moving a knot 461 of a thread 46 of the clip 4 (which will be described later) so as to tighten the thread 46.

The outer tube 6 is composed of a tube body 61 and a hub 62 provided at a proximal end portion of the tube body 61. The clip 4 is detachably mounted to or retained at the distal end portion of the outer tube 6. In this case, the deformation portion 42 (described later) of the clip 4 is retained in a lumen of the distal end portion of the outer tube 6, whereby the clip 4 is mounted.

The hub 62 has a hollow cylindrical tubular portion 621 on the distal side thereof, and a hollow cylindrical tubular portion 622 on the proximal side thereof. The hub 52 of the sheath 5 is adapted to be fitted in the tubular portion 621 of the hub 62, and a tubular portion 721 of a hub 72 of the pusher tube 7 (which will be described later) is adapted to be fitted to the tubular portion 622.

In addition, the hub 62 is provided with an outflow port 623 forming a port for position confirmation. The outflow port 623 has a through-hole which passes through the hub 62 and is communicated with the lumen of the tube body 61. The cap 13 is detachably mounted to the outflow port 623. The cap 13 is in the shape of a pin having a head portion, and is mounted to the outflow port 623 by being inserted into the outflow port 623, whereby the outflow port 623 is closed.

On the other hand, the tube body 61 is provided at its distal end portion with an opening 611 forming an inflow port which communicates with the lumen of the tube body 61. Body fluid (blood) which has flowed through the opening 611 into the lumen of the tube body 61 can flow through a conduit defined or formed by the inside surface of the lumen of the tube body 61 and a groove (not shown) formed in the outside surface of the pusher tube 7, and to flow out via the outflow port 623.

In addition, the length of the outer tube 6 is set to be greater than the length of the sheath 5. As will be described later, when the arrangement device 3 (outer tube 6) is inserted from the proximal side of the sheath 5 into the through-hole 51 of the sheath 5 and the hub 62 of the outer tube 6 and the hub 52 of the sheath 5 are fitted to each other, the distal end portion of the outer tube 6 (a portion inclusive of the opening 611) is exposed from the distal end of the sheath 5 (the distal end of the sheath 5 is located on the proximal side relative to the distal end portion of the outer tube 6).

The pusher tube 7 is composed of a tube body 71, and the hub 72 provided at a proximal end portion 711 of the tube body 71. The purpose of the pusher tube 7 is to push the clip 4, which is mounted to the distal end portion of the outer tube 6, out of the outer tube 6 to release the clip 4. The pusher tube 7 also functions to move the knot 461 of the thread 46 of the clip 4 so as to tighten the thread 46 and to thereby deform the deformation portion 42.

The hub 72 is provided on the distal side thereof with a hollow cylindrical tubular portion 721.

The thread-anchoring cap 9 forming a pulling portion fixing means is detachably mounted to the proximal end portion 711 of the tube body 71. The cap 9 is in the shape of a pin having a head portion, and is mounted to the proximal end portion 711 by being inserted into a lumen of the proximal end portion 711.

With the thread 8 pulled out of the lumen of the proximal end portion 711 to the exterior and with the cap 9 mounted to the proximal end portion 711, the thread 8 is clamped between the cap 9 and the proximal end portion 711, and retained there as shown in FIG. 1. As a result, the thread 8 is anchored to or, relative to, the proximal end portion 711 of the pusher tube 7. In addition, a spherical stopper 47 is attached to one end of the thread 8.

FIG. 1 also illustrates a stopper 12 that is detachably fitted to the tube body 71 of the pusher tube 7. The stopper 12 is composed of a roughly C-shaped mount portion 121, and a grip portion 122. By passing the tube body 71 of the pusher tube 7 through the mount portion 121, the stopper 12 is mounted to the tube body 71 in the vicinity of the hub 72, and is disposed between the hub 72 of the pusher rod 7 and the hub 62 of the outer tube 6.

As shown in FIG. 2, the clip 4 forming a tissue closure is comprised of a clip body 40 (tissue closure body), and the thread 46 forming a first thread member.

The clip body 40 is composed of an anchor portion 41, a deformable deformation portion 42, and a connecting portion 44 connecting the anchor portion 41 and the deformation portion 42 to each other. The anchor portion 41, the deformation portion 42 and the connecting portion 44 (i.e., the entire clip body 40) is preferably molded integrally in one piece of the same material.

The anchor portion 41 is a member having a flat surface portion (flat surface) 412 that is positioned in close contact with around a wound hole (a portion inclusive of the wound hole) from one side surface (inside surface) of the in vivo tissue membrane so as to be anchored and to cover the wound hole and the neighboring portion of the wound hole. In the illustrated embodiment, the anchor portion 41 has a plate-like shape.

As illustrated in FIG. 2, the upper surface of the anchor portion 41 to which the deformation portion 42 is connected is in the shape of a substantially flat surface.

The deformation portion 42 has a pantograph-like shape (e.g., parallelogram shaped)), and is linked or connected to a roughly central portion of the flat surface portion 412 of the anchor portion 41 by way of the connecting portion 44. The pantograph-like shaped deformation portion 42 includes two shorter sides directly connected to the connecting portion 44 and two longer sides directly connected to the shorter sides.

The deformation portion 42 has a frame-like shape which can be deformed between a first form in which it is elongated in a direction substantially perpendicular to the anchor portion 41 and contracted in a direction substantially parallel to the anchor portion 41 and a second form in which it is contracted in a direction substantially perpendicular to the anchor portion 41 and expanded in a direction substantially parallel to the anchor portion 41. Therefore, the deformation portion 42 can be deformed from the fundamental form or shape (initial non-deformed state) shown in FIG. 2 into an arbitrary form between the first form and the second form, such as a form in which it is able to pass through a wound hole and a form in which it is able to close a wound hole by sandwiching an in vivo tissue membrane between the anchor portion 41 and itself from the other side surface (outside surface) of the in vivo tissue membrane.

In the case where the in vivo tissue membrane is a blood vessel wall (living organism lumen wall), the one side surface is the inside surface of the blood vessel wall (living organism lumen), and the other side surface is the outside surface of the blood vessel wall (living organism lumen).

Here, in this embodiment, the deformation portion 42 has a quadrangular annular shape (a polygonal annular shape) formed by a rigid ribbon member (i.e., ribbon-like member) having four bendable portions. Specifically, the deformation portion 42 has a quadrangular shape (quadrangular frame-like shape) having four links integrally formed in one piece and having four corner portions capable of being bent in a hinge-like manner. The deformation portion 42 includes two corner portions 421, 422 at vertically opposed diagonal positions as shown in FIG. 2. The corner portion 422 on the lower side in FIG. 2 (on the side adjacent the anchor portion 41) is linked to a roughly central portion of the flat surface portion 412 of the anchor portion 41 by way of the connecting portion 44, and is made to be an immovable portion which cannot be moved relative to an end portion, on the upper side in FIG. 2, of the connecting portion 44.

This permits the deformation portion 42 to be deformed so that the corner portion 421 and the corner portion 422 come close to and away from each other, i.e., to be deformed in a stretching and contracting manner in two orthogonal directions, and to be swung relative to the anchor portion 41. In addition, when the two corner portions 421, 422 come close to one another, the other pair of corner portions move away from each other. When the two corner portions 421, 422 come away from each other, the other pair of corner portions move closer to one another.

In addition, with respect to the two corner portions 421, 422, the corner portion 421 on the upper side in FIG. 2 (the opposite side of the anchor portion 41) has an upper surface (the surface on the opposite side of the anchor portion 41) formed as a curved convex surface. The corner portion 421 of the deformation portion 42 (an end portion, on the opposite side of the anchor portion 41, of the deformation portion 42) is provided in the vicinity of its center with two holes 425, 428, and the corner portion 422 is provided in the vicinity of its center with two holes 426, 427. In the illustrated embodiment, the holes 425, 428, 426, 427 are through holes.

The connecting portion 44 has a plate-like shape and is provided with a hole 441 in the vicinity of its center. In the illustrated embodiment, the hole 441 is a through hole. By virtue of the connecting portion 44, the anchor portion 41 and the corner portion 422 of the deformation portion 42 can be spaced from each other by a predetermined distance.

The thread 46 is hooked on the side of an end portion (on the opposite side of the anchor portion 41) of the deformation portion 42 and the side of an end portion (on the side of the anchor portion 41) of the deformation portion 42, and is attached to the clip body 40. In this embodiment, the thread 46 is hooked on the corner portion 421 of the deformation portion 42 (the end portion on the opposite side of the anchor portion 41 of the deformation portion 42) and the connecting portion 44 while penetrating the corner portion 421 of the deformation portion 42 and the connecting portion 44. Specifically, the thread 46 passes through or penetrates the hole 425 in the corner portion 421 of the deformation portion 42, the hole 426 in the corner portion 422, and the hole 441 in the connecting portion 44, sequentially from the upper side in FIG. 2, then passes through or penetrates the hole 427 in the corner portion 422, and the hole 428 in the corner portion 421, and forms a knot 461 in the shape as shown in FIG. 3 or 4 on the side of the corner portion 421 (the outside of the deformation portion 42). In addition, a loop 462 through which the thread 8 is to be passed is formed on the upper side, in FIG. 2, of the knot 461. The through holes 425, 426, 427, 428 collectively constitute at least one first through hole in the deformation portion 42. In addition, the through hole 441 in the connecting portion 44 constitutes a second through hole. The thread 46 includes a first part passing through a second one of the first through holes (e.g., hole 427 or 428), and a third part passing through the second through hole 441 in the connecting portion 41, in that order. The first and second parts of the thread 46 which pass through the respective through holes are different, meaning they are not the same thread part. And the third thread part passing through the second through hole 441 is positioned between the first and second parts of the thread 46 along the extent of the thread. Described differently, the thread 46 passes through one of the first through holes 425, through a second one of the first through holes 426, through the second through hole 441, through a third one of the first through holes 427, and through a fourth one of the first through holes 428, in that order. Thus, two different parts of the thread 46 span the interior space bounded by the sides of the frame-shaped deformation portion 42 so that a first part of the thread 46 extends between one of the first through holes 426 and a second one of the first through holes 426, and so that a second part of the thread 46 extends between a third one of the first through holes 427 and a fourth one of the first through holes 428.

The knot 461 ties the thread 46 and can be slid on the thread 46 by applying a force (e.g., a predetermined force or more) in the distal direction. The deformation portion 42 is deformed into a desired form between the first form and the second form, and this condition can be maintained by the knot 461 since the knot 461 is not slid by restoring force of the deformation portion 42. That is, once the deformation portion 42 is deformed into the desired form, the knot 461 maintains the deformation portion in the desired form and prevents the deformation portion from returning to the original non-deformed position or form. When the thread 46 is maintaining the deformation portion 42 is in the desired form, the knot 461 is located at the end portion, on the opposite side of the anchor portion 41, of the deformation portion 42, i.e., at the corner portion 421.

The knot 461 is formed to be larger than the inside diameter of the pusher tube 7, and the loop 462 is formed to be smaller than the inside diameter of the pusher tube 7. This ensures that when the knot 461 of the thread 46 of the clip 4 is slid so as to tighten the thread 46 and thereby deform the deformation portion 42, the loop 462 can enter the lumen of the pusher tube 7, whereas the knot 461 is prevented from entering into the lumen of the pusher tube 7, and the knot 461 can be moved reliably.

As shown in FIGS. 1 and 2, the thread 8 in the state of being passed through the loop 462 of the thread 46 is passed through the lumen of the pusher tube 7, and both end portions of the thread 8 are led out through a proximal end portion 711 of the pusher tube 7 to the exterior. In this condition, with the cap 9 mounted to the proximal end portion 711, the thread 8 is clamped (retained) between the cap 9 and the proximal end portion 711, and is retained at (anchored to) the proximal end portion 711. The clip 4 is retained at one end portion of the thread 8 and, in this condition, the other end portion of the thread 8 is retained at (anchored to) the proximal end portion 711 of the pusher tube 7 by the cap 9.

As a result of this, the clip 4 is inhibited (prevented) from moving toward the distal side. The clip 4 is also inhibited (prevented) from coming off the distal end portion of the outer tube 6.

In the illustrated embodiment, the thread 8 and the thread 46 are separate threads. However, the thread 46 and the thread 8 may be in common with each other.

At least a part of the clip body 40 of the clip 4 is preferably formed of a bioabsorbable material. More preferably, a major part (most part) of the clip body 40 is entirely formed integrally of a bioabsorbable material. This ensures that the major part of the clip body 40 is absorbed into a living organism after a predetermined period of time, and is not left in the living organism, so that influences of the clip body 40 on the human body can be eliminated. In addition, the thread 46 also is preferably formed of a bioabsorbable material.

Examples of the bioabsorbable material to be used include polylactic acid, polyglycolic acid, and polydioxanone, used singly, and complexes thereof. Incidentally, the material constituting the clip body 40 of the clip 4 is not limited to the bioabsorbable material; for example, a biocompatible material such as a resin and a metal can be used for this purpose. Besides, the material constituting the thread 46 is also not limited to the bioabsorbable material.

In addition, as for the physical properties required for the clip body 40 of the clip 4, particularly for the deformation capability of the deformation portion 42, excellent hinge characteristic is desirable. Specifically, a clip body 40 having a tensile strength of 250 to 500 ($Kg/cm^2$), an elongation of 150 to 800%, a tensile modulus of 8 to 20 ($\times 10^3$ $Kg/cm^2$) and a bending strength of 300 to 700 ($Kg/cm^2$) is preferred. By fulfilling these physical property values, the clip body 40 possesses excellent hinge characteristics, and the deformation portion 42 can have a desired deformation capability.

When the arrangement device 3 (body portion 2) is moved in its distal direction relative to the clip 4 while pulling the thread 46 of the clip 4 by the thread 8 in the condition where the clip 4 is off the outer tube 6 as shown in FIG. 11, the knot 461 is pushed in the distal direction by the pusher tube 7, and the knot 461 is moved in the distal direction, whereby the thread 46 is tightened and the deformation portion 42 is deformed.

In this case, when the clip 4 is mounted to the outer tube 6, the deformation portion 42 of the clip 4 is in the form of being elongated in a direction substantially perpendicular to the anchor portion 41 and contracted in a direction substantially parallel to the anchor portion 41 as shown in FIG. 5A. As the knot 461 is moved in the distal direction and the thread 46 is tightened, the corner portion 421 of the deformation portion 42 is gradually moved downward in FIG. 5A and the deformation portion 42 is continuously deformed from the form shown in FIG. 5A to the form shown in FIG. 5B, and then to the form shown in FIG. 5C. In the form shown in FIG. 5C, an in vivo tissue membrane can be clamped between the anchor portion 41 and the deformation portion 42 so as to close up a wound hole. As the deformation portion 42 changes from the form shown in FIG. 5A to the form shown in FIG. 5C, the deformation portion 42 is gradually contracted in a direction substantially perpendicular to the anchor portion 41 and is gradually expanded in a direction substantially parallel to the anchor portion 41.

Since the knot 461 is of such a nature that the knot can be moved only in the distal direction as has been described above, the condition where the deformation portion 42 is in a desired form is maintained by the thread 46.

Thus, according to the clip 4, the degree of deformation of the deformation portion 42 can be regulated (adjusted) continuously, with the distance between the two corner portions 421, 422 being regulated (adjusted) continuously). In the condition where the deformation portion 42 has been set into a desired form, the condition can be maintained. This makes it possible to cope with a variety of situations or cases (i.e., to use the invention with a variety of different conditions of in vivo tissue membranes), such as a person with a thick in vivo tissue membrane, a person with a thin in vivo tissue membrane, a person with a hard in vivo tissue membrane, and a person with a soft in vivo tissue membrane.

The configuration of the clip (tissue closure) is naturally not limited to the particular construction described above and shown in the drawing figures, in as much as it preferably possesses an anchor portion, a deformation portion and a thread (thread member).

For example, the shape of the deformation portion of the clip (tissue closure) is not limited to the generally rectangular configuration shown, and may be other polygons for example, or may be cornerless frame-like shapes such as a circular annular shape and an elliptic annular shape.

A procedure for using the tissue closing device to carry out a stanching (staunching) operation is described below. First, as shown in FIG. 1, the arrangement device 3 is assembled. The stopper 12 is first mounted to the tube body 71 of the pusher tube 7 in the vicinity of the hub 72e, the pusher tube 7 is inserted into the outer tube 6 from the proximal side of the outer tube 6, and the stopper 12 is located between the hub 72 of the pusher tube 7 and the hub 62 of the outer tube 6.

Next, an end portion of the thread 8 is inserted into the pusher tube 7 from the proximal side of the pusher tube 7, and is led out to the exterior via a distal end portion 712 of the pusher tube 7 and a distal end portion of the outer tube 6. Then, the end portion of the thread 8 is passed through the loop 462 of the thread 46 of the clip 4, is inserted into the pusher tube 7 from the distal side of the outer tube 6 and the pusher tube 7, and is led out to the exterior via a proximal end portion 711 of the pusher tube 7.

Subsequently, the deformation portion 42 of the clip 4 is flattened to be deformed into the form shown in FIG. 5A, and the deformation portion 42 is inserted (mounted) into the outer tube 6 from the distal side of the outer tube 6.

Next, while pulling both end portions of the thread toward the proximal side to an appropriate extent, the cap 9 is inserted into the lumen of the proximal end portion 711 of the pusher tube 7, and is mounted there. As a result, both end portions of the thread 8 are clamped between the cap 9 and the proximal end portion 711, to be fixed to the proximal end portion 711, and the distal side relative to both end portions of the thread 8 is disposed in the lumen of the pusher tube 7 along the lumen. The assembly of the arrangement device 3 is thus completed. It is to be recognized that the procedure of assembling the arrangement device 3 is naturally not limited to the above-described procedure.

As the sheath, a sheath ordinarily left indwelling after a treatment for therapy (PCI) or diagnosis (CAG) performed using a catheter is used. A distal end portion of the sheath 5 is inserted in a blood vessel.

Next, as shown in FIG. 1, the arrangement device 3 is gradually inserted into the through-hole 51 of the sheath 5 from the proximal side of the sheath 5, and, as shown in FIG. 6, the hub 62 of the outer tube 6 and the hub 52 of the sheath 5 are fitted to each other. As a result of this, the distal end portion of the outer tube 6 protrudes beyond the distal end portion of the sheath 5, and the anchor portion 41 of the clip 4 protrudes, to be inserted in the blood vessel.

Subsequently, as shown in FIG. 7, the body portion 2 is slowly moved in the direction out of the wound hole so that the anchor portion 41 anchors the clip 4 at the wound hole and a neighboring portion of the wound hole and covers the inside of the blood vessel wall. The anchor portion 41 is thus positioned. As also shown in FIG. 7, the deformation portion 42 and the fixing portion 43 of the clip 4 are moved to the outside of the blood vessel.

During the operation of covering the wound hole and the neighboring portion of the wound hole with the anchor portion 41, when the operator senses a resistance upon the anchor portion 41 touching the wound hole and the surrounding tissues (surface touching resistance) at the time the body portion 2 is moved in the direction pulling the body portion 2 out of the wound hole, it is determined that the anchor portion 41 has abutted on the wound hole and the surrounding tissues (surface abutment) and the positioning of the anchor portion 41 has been completed.

Subsequently, as shown in FIG. 8, the cap 13 mounted to the outflow port 623 of the outer tube 6 is detached. This allows conformation that there is no back flush (flush-back) of blood from the outflow port 623.

In the event the anchor portion 41 is not positioned correctly and the opening 611 of the outer tube 6 is located inside the blood vessel, back flush of blood from the outflow port 623 occurs. In such a case, the cap 13 is mounted to the outflow port 623 so that the covering of the wound hole and the neighboring portion of the wound hole with the anchor portion can be conducted.

Next, as shown in FIG. 9, the stopper 12 present between the hub 62 of the outer tube 6 and the hub 72 of the pusher tube 7 is removed. Then, as shown in FIG. 10, the outer tube 6 or the sheath 5 is moved in the direction of pulling it out of the wound hole, and the hub 72 of the pusher tube 7 and the hub 62 of the outer tube 6 are fitted to each other.

In this case, the deformation portion 42 of the clip 4 retained at a distal end portion of the outer tube 6 is pushed out of the outer tube 6 by the pusher tube 7 to come off, or be pushed out, of the outer tube 6. Subsequently, as shown in FIG. 11, the cap 9 is detached from the proximal end portion 711 of the pusher tube 7.

Next, as shown in FIG. 12, while pulling the thread 8 a little to apply a tension thereto, to thus pull the thread 46 of the clip 4, the body portion 2 is pushed in the direction of inserting it into the wound hole. In this way, as shown in FIG. 5C, the knot 461 is pushed in the distal direction by the pusher tube 7, and the knot 461 is moved in the distal direction, whereby the thread 46 is tightened, and the deformation portion 42 is deformed. This operation is continued until the stanching is completed.

As a result, the deformation portion 42 covers the wound hole and a neighboring portion of the wound hole from the outside of the blood vessel wall. The anchor portion 41 covers the wound hole and a neighboring portion of the wound hole from the inside of the blood vessel wall. The blood vessel wall is thus clamped between the anchor portion 41 and the deformation portion 42, and the wound hole is closed. The condition in which the deformation portion 42 is in the above-mentioned form is maintained by the thread 46.

Finally, as shown in FIG. 13, the body portion 2 and the thread 8 are pulled off, and the clip 4 is disposed (left to indwell) in the living organism. That is, the clip 4 is left behind to indwell in the living organism in the position covering or closing off the wound hole.

Since the stopper 47 is fixed to one end of the thread 8, when the body portion 2 is pulled off, as shown in FIG. 5D, the thread 8 is also pulled off together. By the above operations, the stanching operation is completed.

As has been described above, with the disclosed tissue closing device 1, in the condition where the deformation portion 42 of the clip 4 has been brought into a desired form or condition between the first form and the second form, the condition can be maintained by the thread 46. This makes it possible to cope with a variety of conditions of in vivo tissue membranes, and to apply a stanching operation to a wound hole formed in an in vivo tissue membrane such as a blood vessel wall relatively easily and reliably. Namely, it is possible to close or cover the wound hole relatively easily and reliably, and to achieve an effective stanching.

In addition, the deformation portion 42 can be deformed relatively easily and reliably. Therefore, if a failure in stanching has occurred, the deformation portion 42 is then assuredly spreading in the direction substantially parallel to the anchor portion 41, so that manual astriction can thereafter be conducted. Accordingly, the stanching operation can be carried out quite safely.

In addition, since the thread 8 is formed as a member different from the thread 46, an operation of cutting the thread within the subcutaneous tissues is not required. Therefore the stanching operation is performed relatively easily and swiftly.

Further since the thread 46 of the clip 4 is hooked on the corner portion 421 of the deformation portion 42 and the connecting portion 44, there is an additional benefit in that the thread 46 does not have to enter into the blood vessel.

A second embodiment of the tissue closing device according to the present invention will now be described below with reference to FIG. 14.

For convenience, in the following description, in FIG. 14 the upper side will be referred to as "proximal" and the lower side will be referred to as "distal." Also, the following detailed description of the second embodiment will primarily describe differences associated with the second embodiment relative to the first embodiment, and a detailed description of features in the second embodiment that are similar to those in the first embodiment will not be repeated.

In the tissue closing device 1 according to the second embodiment, the clip (tissue closure) 4 differs from the clip 4 in the first embodiment described above, with the remaining features of the second embodiment being generally the same as in the first embodiment.

As shown in FIG. 14, in the second embodiment, a thread 46 of the clip 4 is hooked on a corner portion 421 of the deformation portion 42 (an end portion of the deformation portion 42 on the opposite side of an anchor portion 41) and on the anchor portion 41. In the illustrated embodiment, the thread 46 penetrates the corner portion 421 of the deformation portion 42 and the anchor portion 41. The anchor portion 41 of the clip 4 is provided, in the vicinity of its center, with two holes 413, 414 opposite to each other, with the connection portion 44 between the two holes. In the illustrated embodiment, the holes 413, 414 are through holes. The thread 46 passes through (penetrates) the hole 425 in the corner portion 421 of the deformation portion 42, the hole 426 in the corner portion 422 and the hole 413 in the anchor portion 41, sequentially from the upper side in FIG. 14, and then passes through the hole 414 in the anchor portion 41, the hole 427 in the corner portion 422, and the hole 428 in the corner portion 421, and forms a knot 461 on the side of the corner portion 421 (on the outside of the deformation portion 42).

According to this tissue closing device 1, the same effects as those of the tissue closing device in the first embodiment described above can be obtained.

In this version of the clip used in the tissue closing device 1, since the thread 46 of the clip 4 is hooked on the corner portion 421 of the deformation portion 42 and the anchor portion 41, even if the connecting portion 44 is cut at the time of a stanching operation, the anchor portion 41 can be inhibited (prevented) from flowing into the blood vessel.

In addition, since the connecting portion 44 is provided with no hole through which to pass the thread 46, the strength of the connecting portion 44 can be enhanced as compared with the first embodiment.

A third embodiment of the tissue closing device according to the present invention will now be described below with reference to FIG. 15.

For convenience, in the following description, in FIG. 15 the upper side will be referred to as "proximal" and the lower side will be referred to as "distal." Also, the following detailed description of the third embodiment will primarily describe differences associated with the third embodiment relative to the first embodiment, and a detailed description of features in the third embodiment that are similar to those in the first embodiment will not be repeated.

In the tissue closing device 1 according to the third embodiment, the clip (tissue closure) 4 differs from the clip 4 in the first embodiment described above, with the remaining features of the third embodiment being generally the same as in the first embodiment.

As shown in FIG. 15, the third embodiment includes a plate-like thread hook portion 45 on the inside surface of the corner portion 422 of the deformation portion 42 of the clip 4 (the inside surface of the deformation portion 42 on the side of the anchor portion 41). The thread hook portion 45 is provided with a hole 451 in the vicinity of its center. In the illustrated embodiment, the hole 451 is a through hole. In addition, the anchor portion 41, the deformation portion 42, the connecting portion 44 and the thread hook portion 45 (i.e., the entire clip body 40) is preferably formed integrally in one piece of the same material.

The thread 46 of the clip 4 is hooked on a corner portion 421 of the deformation portion 42 (an end portion of the deformation portion 42 on the opposite side of the anchor portion 41) and the thread hook portion 45. In the illustrated embodiment, the thread 46 penetrates the corner portion 421 of the deformation portion 42 and the hole 451 in the thread hook portion 45. Specifically, the thread 46 passes through (penetrates) the hole 425 in the corner portion 421 of the deformation portion 42, and the hole 451 in the thread hook portion 45, sequentially from the upper side in FIG. 15, and then passes through (penetrates) the hole 428 in the corner portion 421, and forms a knot 461 on the side of the corner portion 421 (on the outside of the deformation portion 42).

This tissue closing device 1 using the clip shown in FIG. 15 is capable of achieving the same effects as those of the tissue closing device 1 in the first embodiment described above.

In the tissue closing device 1 using the clip shown in FIG. 15, since the thread 46 of the clip 4 is hooked on the corner portion 421 of the deformation portion 42 and the thread hook portion 45, whereas the connecting portion 44 is provided with no hole through which to pass the thread 46, the strength of the connecting portion 44 can be enhanced as compared with the first embodiment.

A fourth embodiment of the tissue closing device according to the present invention will now be described below with reference to FIGS. 16 and 17(a)-(d). In addition to illustrating the clip used in this embodiment, FIG. 17(d) also schematically illustrates a pusher tube 7 in broken lines.

For convenience, in the following description, in FIGS. 16 and 17(a)-(d) the upper side will be referred to as "proximal" and the lower side will be referred to as "distal." Also, the following detailed description of the fourth embodiment will primarily describe differences associated with the fourth embodiment relative to the first embodiment, and a detailed description of features in the fourth embodiment that are similar to those in the first embodiment will not be repeated.

In the tissue closing device 1 in the fourth embodiment, the clip (tissue closure) 4 and the pusher tube 7 are respectively different from the clip 4 and the pusher tube 7 in the first embodiment described above, and the other aspects of are generally the same as in the first embodiments.

As shown in FIGS. 16 and 17(a)-(d), in the fourth embodiment, the clip body 40 of the clip 4 is composed of the anchor portion 41, the deformation portion 42, the connecting portion 44 connecting the anchor portion 41 and the deformation portion 42 to each other, and a fixing portion 43 which, in the condition where the deformation portion 42 is in a desired form between a first form and a second form, is engaged with the deformation portion 42 so as to maintain the condition. The anchor portion 41, the deformation portion 42, the connecting portion 44 and the fixing portion 43 (i.e., the entire clip body 40) are preferably formed integrally of the same material.

The deformation portion 42 is provided with a roughly H-shaped slit 424 at its corner portion 421 (an end portion of the deformation portion 42 on the opposite side of the anchor portion 41). The slit 424 is an opening portion which penetrates the frame-like deformation portion 42 and which permits at least a part of the fixing portion 43 to be inserted therein (i.e., to be passed therethrough).

The fixing portion 43 has a plate-like (rod-like) shape. The fixing portion 43 is located inside the frame of the deformation portion 42, and its end portion on the lower side in FIG. 16 is linked to the inside surface of a corner portion 422. This ensures that the fixing portion 43 can be swung relative to the anchor portion 41, together with the deformation portion 42.

In addition, the fixing portion 43 is provided with pawls 431 on one side (right side) in the left-right direction in FIG. 16. The pawls 431 are preferably plural in number (two, in the example shown) and are positioned side by side at a predetermined spacing from one another along the longitudinal direction of the fixing portion 43 (vertical direction in FIG. 16).

The fixing portion 43 is also provided with a hole 432 in the vicinity of the center of its end portion on the upper side in FIG. 16 (an end portion of the fixing portion 43 on the opposite side of the anchor portion 41). In the illustrated embodiment, the hole 432 is a through hole.

As shown in FIG. 16, when the fixing portion 43 is not inserted or positioned in the slit 424, the thread 46 of the clip 4 is hooked on the corner portion 421 of the deformation portion 42 (the end portion of the deformation portion 42 on the opposite side of the anchor portion 41) and the fixing portion 43 while penetrating the slit 424 in the corner portion 421 of the deformation portion 42 and the hole 432 in the fixing portion 43. Specifically, the thread 46 passes through (penetrates) the slit 424 in the corner portion 421 of the deformation portion 42 and through the hole 432 in the fixing portion 43, sequentially from the upper side in FIG. 16, then passes through (penetrates) the slit 424 in the corner portion 421, and forms a knot 461 on the side of the corner portion 421 (on the outside of the deformation portion 42). The knot 461 is formed to be greater in size than the gap (the dimension in the left-right direction in FIG. 16) of the slit 424.

As shown in FIG. 17(d), the inside diameter of the lumen of the distal end portion 712 of the pusher tube 7 is set to be greater than the inside diameter of the lumen at a location on the proximal side relative to the distal end portion 712. The inside diameter of the lumen of the distal end portion 712 is greater than the fixing portion 43 of the clip 4.

Here, the maintaining function of the thread 46 and the maintaining function of the fixing portion 43 are selectively performed according to the degree of deformation of the deformation portion 43 between the first form and the second form. With the first form of the deformation portion 42 as a reference, in the region where the degree of deformation of the deformation portion 42 is small, the condition where the deformation portion 42 is in a desired form is maintained by the thread 46. On the other hand, in the region where the degree of deformation of the deformation portion 42 is large, the condition where the deformation portion 42 is in a desired form is maintained by the fixing portion 43.

When an arrangement device 3 (body portion 2) is moved in the distal direction thereof relative to the clip 4 while pulling the thread 46 of the clip 4 by a thread 8 in the condition where the clip 4 is off the outer tube 6, the distal end portion 712 of the pusher tube 7 touches the upper surface 423 of the corner portion 421 of the deformation portion 42 from the upper side in FIGS. 17(a)-(d), and the knot 461 is pushed in the distal direction by the pusher tube 7. The knot 461 is thus moved in the distal direction, the thread 46 is tightened, and the deformation portion 42 is deformed.

In this case, when the clip 4 is being mounted to the outer tube 6, the deformation portion 42 is in the form of being stretched in a direction substantially perpendicular to the anchor portion 41 and contracted in a direction substantially parallel to the anchor portion 41, as shown in FIG. 17(a). Then, as the knot 461 is moved in the distal direction and the thread 46 is tightened, the corner portion 421 of the deformation portion 42 is gradually moved downward in FIG. 17(a), so that the deformation portion 42 is deformed continuously from the form shown in FIG. 17(a) to the form shown in FIG. 17(b). In addition, since the knot 461 is such a knot that it can slide toward the distal direction, the condition where the deformation portion 42 is in a desired form is maintained by the thread 46.

Then, when the arrangement device 3 (body portion 2) is moved further in the distal direction thereof relative to the clip 4 while pulling the thread 46 of the clip 4 by the thread 8, the corner portion 421 of the deformation portion 42 is pushed downward in FIG. 17(b) by the pusher tube 7. In this instance, the fixing portion 43 is located inside the lumen of the pusher tube 7, and does not constitute an obstacle as illustrated in FIG. 17(c).

As a result, as shown in FIG. 17(c), the corner portion 421 of the deformation portion 42 is moved downward, an end portion on the upper side of the fixing portion 43 and the pawl 431 on the upper side of the fixing portion 43 pass through (are inserted into) the slit 424 formed in the corner portion 421, and the pawl 431 is engaged with the corner portion 421. In this instance, the thread 46 located on the inside of the deformation portion 42 is moved to the outside of the deformation portion 42 via the slit 424, together with the hole 432 in the fixing portion 43.

Even if the pushing force applied by the pusher tube 7 is canceled at this point, the condition where the deformation portion 42 is in a desired form (i.e., the shape of the deformation portion 42) is maintained by the fixing portion 43. In addition, even if the corner portion 421 of the deformation portion 42 is pushed upward in FIG. 17(d), the condition where the deformation portion 42 is in the desired form is maintained by the fixing portion 43.

When the arrangement device 3 (body portion 2) is moved further in the distal direction thereof relative to the clip 4, the corner portion 421 of the deformation portion 42 is pushed further downward in FIG. 17(d) by the pusher tube 7.

As a result of this, the corner portion 421 of the deformation portion 42 is moved further downward in FIG. 17(d), the pawl 431 on the lower side in FIG. 17(d) of the fixing portion 43 passes through (is inserted into) the slit 424 formed in the corner portion 421, and the pawl 431 is engaged with the corner portion 421.

Even if the pushing force applied by the pusher tube 7 is canceled at this time, the condition where the deformation portion 42 is in a desired form is maintained by the fixing portion 43 in the same manner as described above.

According to the tissue closing device 1 using this clip and pusher tube, the same effects as those of the tissue closing device 1 in the first embodiment described above can be obtained.

In this tissue closing device 1, since the condition where the deformation portion 42 is in a desired form is maintained by the fixing portion 43, the condition where the deformation portion 42 is in the desired form can be maintained more firmly as compared with the first embodiment.

In addition, even in the situation where the deformation portion 42 is not deformable (is not deformed) to such an extent that the pawl 431 of the fixing portion 43 is engaged with the corner portion 421 of the deformation portion 42, the deformation portion 42 can be maintained in the desired form by the thread 8.

Since the thread 46 of the clip 4 is hooked on the corner portion 421 of the deformation portion 42 and the fixing portion 43 and the connecting portion 44 is provided with no hole through which to pass the thread 46, the strength of the connecting portion 44 can be made increased as compared with the first embodiment.

It is to be understood that the number of pawl(s) provided on the fixing portion of the clip (tissue closure) is not limited to two, but may be one in number or may be three or more.

A fifth embodiment of the tissue closing device will be described below with reference to FIGS. 18(a)-(b) and 19(a)-(b). These drawing figures schematically illustrate a pusher tube 7 in broken lines. In addition, a knot 461 of a thread 46 is shown in the state of not being tied tightly.

In the following description, in FIGS. 18(a)-(b) and 19(a)-(b) the upper side will be referred to as "proximal" and the lower side will be referred to as "distal." Also, the following detailed description of the fifth embodiment will primarily describe differences associated with the fifth embodiment relative to the first embodiment, and a detailed description of features in the fifth embodiment that are similar to those in the first embodiment will not be repeated.

In the tissue closing device 1 according to the fifth embodiment, the thread (first thread member) 46 of the clip (tissue closure) 4 and the thread (second thread member) 8 are respectively different from the thread 46 of the clip 4 and the thread 8 in the first embodiment described above. In addition, a thread lock member (fixture) 14 is provided. The remaining features associated with this embodiment of the tissue closing device are similar to those associated with the first embodiment of the tissue closing device.

As shown in FIGS. 18(a)-(b) and 19(a)-(b), in the fifth embodiment, the thread (first thread member) 46 of the clip 4 is composed of a double thread (double thread member) formed by bending back a single thread (thread member) so that one end portion constitutes a bent-back portion 463, and the bent-back portion 463 forms a loop 462. In addition, a deformation portion 42 is located between the bent-back portion 463 (loop 462) and an anchor portion 41.

The thread (second thread member) 8 is composed of a double thread (double thread member) formed by bending back a single thread (thread member) so that one end potion constitutes a bent-back portion 81. A hollow cylindrical stopper 47 is fixed to the other end portion of the thread 8. The stopper 47 may be fixed by, for example, adhesion, caulking or the like. The tissue closure 4 is detachably retained by the thread 8. In addition, the stopper 47 inhibits (prevents) an end portion, on the opposite side of the bent-back portion 81, of the thread 8 from entering into the lumen of the pusher tube 7.

The thread lock member (fixture) 14 is composed of a filamentous member having a head portion as shown in FIG. 19(a), and can be elastically deformed into a bent or curved shape, as shown in FIGS. 18(a) and 18(b). The thread lock member 14 may be formed, for example, from a resin material or the like.

As shown in FIGS. 18(*a*) and 18(*b*), the bent-back portion 81 of the thread 8 is located at a proximal end portion 711 of the pusher tube 7. The thread lock member 14 is disposed at the proximal end portion 711 of the pusher tube 7 in the state of being bent or curved by being hooked on the bend-back portion 81 of the thread 8.

It should be noted that the head portion side and the distal end side of the thread lock member 14 are both positioned in the outside of the pressure tube 7.

At the time of deforming the deformation portion 42 in a stanching operation, as shown in FIG. 18(*b*), the stopper 47 is gripped by fingers of a hand, and while pulling the stopper 47 (thread 8) a little so as to apply a tension to a thread 8 (thereby pulling the thread 46 of the clip 4), the pusher tube 7 (body portion 2) is pushed in the direction of inserting it into a wound hole. In this instance, by the presence of the thread lock member 14, the bent-back portion 81 of the thread 8 can be inhibited (prevented) from moving in the distal direction inside the lumen of the pusher tube 7, whereby the thread 46 of the clip 4 can be pulled assuredly.

At the time of pulling off the body portion 2 and the thread 8, the thread lock portion 14 is detached as shown in FIG. 19(*a*), and the pusher tube 7 (body portion 2) is pulled off as shown in FIG. 19(*b*), whereupon the thread 8 is also pulled off together.

According to this tissue closing device 1, the same effects as those of the tissue closing device 1 in the first embodiment described above can be obtained.

In addition, in this tissue closing device 1, since the loop 462 is formed by the bent-back portion 463 of the thread 46, the work of assembling the clip 4 and the operation of pushing the knot 461 by the pusher tube 7 so as to deform the deformation portion 42 can be performed easily and swiftly, as compared with the case where a knot other than the knot 461 is tied in the thread 46 and is used as a loop. The reason is as follows. In the case where a knot other than the knot 461 is formed and is used as a loop, at the time of deforming the deformation portion 42 in a stanching operation, it is necessary to push only the knot 461 without pushing the new knot constituting the loop, which means very severe conditions for the operation.

In addition, at the time of pulling off the thread 8, the side of the bent-back portion 81 of the thread 8 may once enter into a living organism. In the tissue closing device 1, however, the bent-back portion 81 and the portions near the bent-back portion 81 of the thread 8 can be located in the lumen of the pusher tube 7, so that a sterile condition can be maintained, and the stanching operation can be performed quite safely.

Also, in this tissue closing device 1, at the time of pulling off the thread 8, the thread 8 can be passed through the loop 462 of the thread 46 more smoothly and the loop 462 of the thread 46 can be moved in the lumen of the pusher tube 7 more smoothly, as compared with the case where a knot other than the knot 461 is formed and is used as a loop.

It is to be understood that the fifth embodiment can be applied also to the second to fourth embodiments described above.

A sixth embodiment of the tissue closing device according to the present invention will be described below with reference to FIGS. 20 and 21. For convenience of description, in FIGS. 20 and 21 the upper side will be referred to as "proximal" and the lower side will be referred to as "distal". Also, the following detailed description of the sixth embodiment will primarily describe differences associated with the sixth embodiment relative to the first embodiment, and a detailed description of features in the sixth embodiment that are similar to those in the first embodiment will not be repeated.

In the tissue closing device 1 in the sixth embodiment, an anchor portion 410 is different from the anchor portion 41 in the first embodiment described above, and the other points are the same as in the first embodiment.

As shown in FIG. 20, in the sixth embodiment, the anchor portion 410 is connected to the connection portion 44 on an eccentric position of a flat surface portion 415 of the anchor portion 410. The connection position is to the right side beyond a center position of the flat surface portion 415 as shown in FIG. 20. Thus, the connection portion 44 is connected to the anchor portion 410 at a position offset from a center point of the anchor portion 410.

The length of a left-side portion a of the flat surface portion 415 is longer than the length of a right-side portion b of the flat surface portion 415. Here, the total length of the anchor portion 410 is equal to the total length of the anchor portion in the first embodiment.

As shown in FIG. 21, in the sixth embodiment, the longer portion a of the anchor portion 41 is arranged upstream of blood flow (a side of a heart) and the shorter portion b of the anchor portion 41 is arranged downstream of blood flow (a side of a peripheral) when the anchor portion 41 is positioned in a blood vessel.

Thus, when the closing device 1 is drawn out, the resistance of the blood vessel wall increases and it is difficult for the anchor portion 410 to escape. Because the closing device 1 which is being drawn out generates the strongest resistance on a portion that is the acute angle side of the anchor portion 41 with the blood vessel and the closing device 1 (i.e., the right side in FIG. 21), the effect of the resistance can be distributed by changing the balance of the anchor (i.e., by positioning the longer portion b of the anchor to the obtuse angle side of the anchor portion 41).

The features described in connection with the sixth embodiment can be applied also to the second to fifth embodiments discussed above.

While the tissue closure and the tissue closing device herein have been described above based on the embodiments shown in the drawings, the present invention is not limited to or by these embodiments, and the configurations of the individual portions can be replaced by other configurations that have the same or similar functions as discussed above. Also, other components or structures may be added to the present invention.

In addition, the present invention may be embodied in a combination of two or more configurations (characteristic features) of the above-described embodiments.

Furthermore, in the above embodiments, the deformation portion 42 has a frame-like shape which can be deformed between the first form of being elongated in a direction substantially perpendicular to the anchor portion 41 and contracted in a direction substantially parallel to the anchor portion 41 and the second form of being contracted in a direction substantially perpendicular to the anchor portion 41 and expanded in a direction substantially parallel to the anchor portion 41. In the present invention, however, the deformation portion is not limited to this configuration, and may have any configuration inasmuch as it can be deformed into a form (first form) of being elongated in a direction substantially perpendicular to an anchor portion and a form (second form) of being compressed from this form (first form) toward the anchor portion. In other words, other than those in the above embodiments, the deformation portion can be composed, for example, of a spongy porous member (porous material) containing a resin material (synthetic resin material) as a main material, or the like. Also, while the description above refers to a thread member(s) (thread(s)), it is to be understood that such term encompasses thread-like members.

The principles, preferred embodiments and manners of use of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A tissue closure for closing a punctured portion on a wall of a blood vessel, comprising:
    a plate-shaped anchor portion adapted to be held at and around the punctured portion from one side of the wall of the blood vessel;
    a deformation portion comprising a frame-shaped body, the deformation portion being deformable between a first form in which the body is elongated in a direction substantially perpendicular to the anchor portion and contracted in a direction substantially parallel to the anchor portion and a second form in which the body is contracted in a direction substantially perpendicular to the anchor portion and elongated in a direction substantially parallel to the anchor portion;
    the deformation portion comprising a plurality of first through holes;
    a thread member adapted to maintain the deformation portion in a desired form between the first form and the second form;
    a connecting portion connecting the anchor portion and the deformation portion to each other, and the anchor portion being movable relative to the connecting portion to vary an angle between the plate-shaped anchor portion and the plate shaped connecting portion;
    the thread member comprising a first part passing through one of the first through holes in the deformation portion and a second part passing through another hole of the plurality of first through holes in the deformation portion;
    the connecting member or the anchor portion being provided with a second through hole through which passes a third part of the thread member, the third part being positioned between the first and second parts along the extent of the thread member; and
    the thread member passing through the one of the plurality of first through holes, through the second through hole, and through the another hole of plurality of first through holes in that order.

2. The tissue closure according to claim 1, wherein the frame-shaped body of the deformation portion possesses a pantograph-like shape.

3. The tissue closure according to claim 1, wherein the frame-shaped body of the deformation portion possesses a polygonal annular shape formed by a rigid ribbon member having a plurality of bendable portions.

4. The tissue closure according to claim 1, wherein the frame-shaped body of the deformation portion possesses a quadrangular shape formed by four integrated links and is deformable so that two corner portions at diagonally opposite positions move towards and away from one another as the deformation portion deforms between said first and second forms.

5. The tissue closure according to claim 1, wherein said thread member comprises a knot slidable on the thread member, the knot maintaining the deformation portion in the desired form.

6. The tissue closure according to claim 5, wherein when the thread member is maintaining the deformation portion in the desired form, the knot is located at a first end portion on a side of the deformation portion opposite the anchor portion.

7. The tissue closure according to claim 1, wherein the thread member is hooked on one end portion of the deformation portion at a side opposite the anchor portion and is hooked on a another end portion of the deformation portion at a side closer to the anchor portion.

8. The tissue closure according to claim 1, wherein the anchor portion, the connecting portion and the deformation portion are integrally formed in one piece of the same material.

9. The tissue closure according to claim 1, wherein the thread member is hooked on one end portion of the deformation portion on a side opposite the anchor portion and the connecting portion, the thread member penetrating the deformation portion and the connecting portion.

10. The tissue closure as set forth in claim 1, wherein at least one of said anchor portion, said deformation portion and said thread member is comprised of a bioabsorbable material.

11. The tissue closure according to claim 1, wherein the deformation portion includes at least three first through holes.

12. The tissue closure according to claim 11, wherein two of the first through holes are on one end of the deformation portion, and the other first through hole is on an opposing end of the deformation portion.

13. The tissue closure according to claim 11, wherein a part of the thread member passes through the three first through holes.

14. The tissue closure according to claim 1, wherein the second through hole is in the connecting member, and spaced apart third parts of the thread member pass through respective spaced apart additional first through holes in the deformation portion.

15. A tissue closing device, comprising:
    a tissue closure comprising an anchor portion, a connecting portion, a deformation portion and a thread member;
    the anchor portion being positionable at and around a punctured portion on one side of a blood vessel;
    the deformation portion being deformable between a first form in which the deformation portion is elongated in a direction substantially perpendicular to the anchor portion and a second form in which the deformation portion is compressed from the first form toward the anchor portion, the deformation portion possesses a polygonal annular shape formed by a rigid ribbon member having a plurality of bendable portions;
    the deformation portion comprising two spaced apart first through holes;
    the connecting portion connecting the anchor portion and the deformation portion to each other, the connecting portion being configured to permit the anchor portion to move relative to the connecting portion;
    the connecting portion, the anchor portion and the deformation portion being integrally formed in one piece of the same material;
    the thread member maintaining the deformation portion in a desired form between the first form and the second form;
    an arrangement device possessing an elongate shape, the arrangement device detachably retaining the tissue closure at a distal end portion thereof;

the tissue closure being adapted to be arranged in a living organism so as to close the punctured portion by penetrating a tissue membrane of the blood vessel wall with the tissue closure;

the connecting member possessing a second through hole;

the thread member passing through one of the first through holes, through the second through hole in the connecting member, and through the other first through hole in that order.

16. The tissue closing device according to claim 15, wherein the deformation portion is frame-shaped and includes a plurality of links and a plurality of corners, with each corner connecting two adjacent links, the two first through holes being located in one of the corners.

17. The tissue closure according to claim 16, further comprising two spaced apart third through holes in the corner of the frame-shaped deformation portion located diagonally opposite the one corner.

18. A tissue closure for closing a punctured portion on a wall of a blood vessel, comprising:

a plate-shaped anchor portion adapted to be held at and around the punctured portion from one side of the wall of the blood vessel;

a deformation portion comprising a frame-shaped body, the deformation portion being deformable between a first form in which the body is elongated in a direction substantially perpendicular to the anchor portion and contracted in a direction substantially parallel to the anchor portion and a second form in which the body is contracted in a direction substantially perpendicular to the anchor portion and elongated in a direction substantially parallel to the anchor portion;

a thread member adapted to maintain the deformation portion in a desired form between the first form and the second form;

a plate-shaped connecting portion connecting the plate-shaped anchor portion to the deformation portion, the connection between the plate-shaped connecting portion and the plate-shaped anchor portion permitting the plate-shaped anchor portion to move relative to the connecting portion to vary an angle between the connecting portion and the anchor portion;

the connecting portion, the anchor portion and the deformation portion being integrally formed in one piece of the same material;

the deformation portion being frame-shaped with a wall surrounding an interior space;

the wall of the deformation portion being provided with four spaced apart first through holes;

the connection portion being provided with a second through hole;

the thread member passing through one of the first through holes, through a second one of the first through holes, through the second through hole, through a third one of the first through holes and through a fourth one of the first through holes in that order; and two different parts of the thread member spanning the interior space so that a first part of the thread member extends between the one first through hole and the second of the first through holes, and a second part of the thread member extends between the third one of the first through holes and the fourth one of the through holes.

19. The tissue closing device according to claim 18, wherein the frame-shaped deformation portion includes a plurality of links and a plurality of corners, with each corner connecting two adjacent links, the other first through hole and the third first through hole being located in one of the corners, the one first through hole being located in the corner diagonally opposite the one corner.

20. The tissue closing device according to claim 19, wherein the corner diagonally opposite the one corner includes another first through hole.

* * * * *